(12) United States Patent
Tanaka et al.

(10) Patent No.: US 6,461,304 B1
(45) Date of Patent: Oct. 8, 2002

(54) ULTRASOUND INSPECTION APPARATUS DETACHABLY CONNECTED TO ENDOSCOPE

(75) Inventors: Toshizumi Tanaka; Hiromu Itoi; Toshio Sakamoto; Masatoshi Yoshihara; Shinichi Kohno, all of Omiya (JP)

(73) Assignee: Fuji Photo Optical Co., Ltd., Omiya (JP)

( * ) Notice: Subject to any disclaimer, the term of this patent is extended or adjusted under 35 U.S.C. 154(b) by 0 days.

(21) Appl. No.: 09/667,176

(22) Filed: Sep. 21, 2000

(30) Foreign Application Priority Data

| Mar. 30, 1999 | (JP) | 11-278193 |
| Sep. 22, 1999 | (JP) | 11-268251 |
| Sep. 24, 1999 | (JP) | 11-270323 |
| Sep. 27, 1999 | (JP) | 11-271688 |
| Sep. 28, 1999 | (JP) | 11-273624 |

(51) Int. Cl.[7] ............................................... A61B 8/14
(52) U.S. Cl. ..................................................... 600/462
(58) Field of Search ............................... 600/459–467, 600/117, 118, 141; 128/916, 899

(56) References Cited

U.S. PATENT DOCUMENTS

| 4,757,819 A | * 7/1988 | Yokoi et al. ................. 600/141 |
| 5,131,393 A | 7/1992 | Ishiguro et al. |
| 5,131,396 A | 7/1992 | Ishiguro et al. |
| 5,150,715 A | 9/1992 | Ishiguro et al. |
| 5,211,176 A | 5/1993 | Ishiguro et al. |
| 5,257,628 A | 11/1993 | Ishiguro et al. |
| 5,680,865 A | 10/1997 | Tanaka |

\* cited by examiner

Primary Examiner—Marvin M. Lateef
Assistant Examiner—Ali M. Imam
(74) Attorney, Agent, or Firm—Oblon, Spivak, McClelland, Maier & Neustadt, P.C.

(57) ABSTRACT

An ultrasound inspection apparatus detachably connected to an endoscope comprises an ultrasonic scanning portion in the front-end side having an ultrasound transducer for performing ultrasonic scanning by arranging a number of transducer chips in a rectangular arrangement. The ultrasonic scanning portion is detachably attached to a distal end portion of an insertion unit in the endoscope so as to protrude ahead the distal end portion by a predetermined length. In order to hold the ultrasonic scanning portion in a fixed state, an endoscope-placing portion for placing the distal end portion is connected to the base end of the ultrasonic scanning portion, and an endoscope-fixing portion for detachably fixing the distal end portion thereto is arranged with the endoscope-placing portion. A predetermined number of wires connected to each transducer chip is inserted into a signal cable from a base end position of the endoscope-placing portion so as to bundle the wires.

16 Claims, 17 Drawing Sheets

F I G. 1
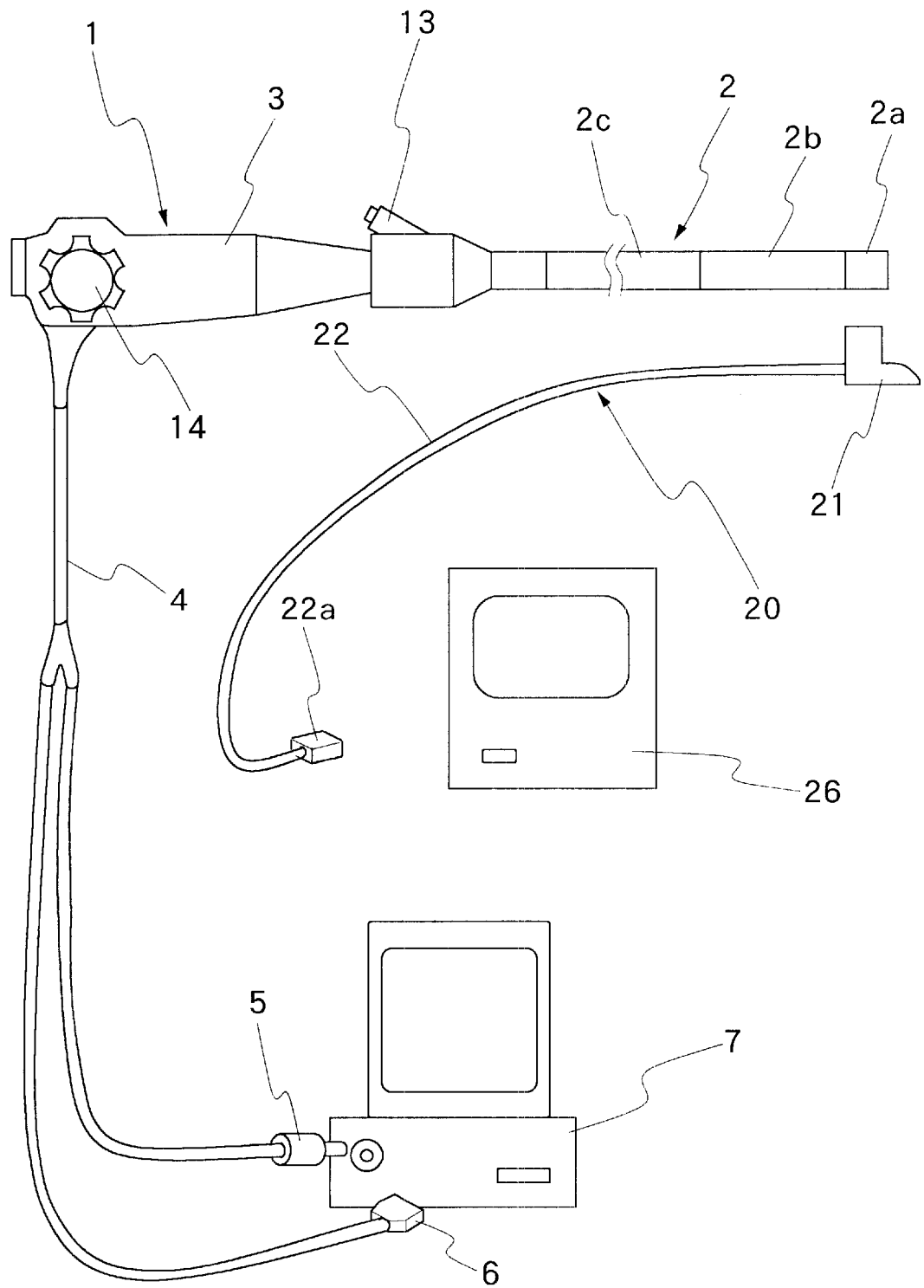

ULTRASOUND INSPECTION APPARATUS DETACHABLY CONNECTED TO ENDOSCOPE

DETAILED DESCRIPTION OF THE INVENTION

1. Field of the Invention

The present invention relates to an ultrasound inspection apparatus detachably connected to an endoscope.

2. Description of the Prior Art

Typical apparatuses for performing required inspection or diagnosis by inserting them into a body to be inspected include an endoscope for observing the inside of a body cavity and an ultrasound inspection apparatus for obtaining information about textures inside a body. An ultrasound endoscope unitarily combining the endoscope with the ultrasound inspection apparatus is also known. For example, as disclosed in Japanese Unexamined Patent Application Publication No. 8-52138, a known ultrasound endoscope is formed so that an ultrasonic scanning portion having an ultrasound transducer attached thereto is arranged at a distal end portion of an insertion unit and an inclined wall surface is formed in the base side of the ultrasonic scanning portion so as to form illuminating means and observing means forming an endoscope observing structure therein. On the inclined wall surface, a treating instrument guide channel is also provided for leading out a puncture instrument, etc., for puncturing within a field of ultrasound observing vision by the ultrasound transducer.

In such a manner, using of the ultrasound endoscope enables to inspect an inner wall of a body cavity and the like, with an endoscopic observing unit by inserting the insertion unit to a predetermined position. When disease or the like is discovered by observation with the endoscope, the state of textures inside the body, etc., can be inspected by operating the ultrasound transducer so as to perform ultrasonic scanning of the portion in question. From the result of the ultrasonic scanning, when medical treatment or sampling of texture, etc., is required, an appropriate operation can be taken by inserting a puncture instrument through the guide channel under observation by the ultrasound transducer.

In the ultrasound endoscope of the type, the ultrasonic observing means is undetachably formed in combination with endoscope observing means undetachably, and it is suitable for using in the case of combining endoscopic inspection with ultrasound inspection. However, since the ultrasonic observing means is located in front of the endoscope observing means in the ultrasound endoscope, the field of view by the endoscope observing means is extremely limited. A treating instrument outlet portion is arranged at the position of the endoscopic observing means, so that operations of treating instruments are also limited. By these reasons, the ultrasound endoscope is not generally used when it is only for the endoscopic inspection.

A structure is known in that, when required, ultrasound inspection can be used in combination with endoscopic inspection without limiting the function as an endoscope. For example, Japanese Unexamined Patent Application Publication No. 11-42231 discloses a so-called ultrasound probe inserted through an endoscope that is formed to be led into body cavities, etc., by inserting into an guide channel for inserting treating instruments of an endoscope. The ultrasonic probe of the type is formed of an ultrasonic scanning unit provided with an ultrasound transducer, a flexible cord arranged in line with the ultrasonic scanning unit, and a connector disposed at the base end of the flexible cord. The flexible cord is to be inserted through the guide channel for inserting treating instruments of an endoscope. The connector disposed at the base end of the flexible cord is formed to be detachably connected to the ultrasonic scanning unit directly or through a connecting adapter, etc. The ultrasonic scanning unit includes operating means for scanning the ultrasound transducer in a rotating direction or an axial direction.

In the ultrasonic probe inserted through the endoscope, the transducer placed in the ultrasonic scanning unit are formed of single-chip transducer so as to scan mechanically in a rotating direction or a linear direction. When large-sized transducer chip is provided by using the ultrasonic scanning unit having a larger diameter than the inner diameter of the treating instrument guide channel, from front-end of the treating instrument guide channel, the ultrasound probe is inserted thereinto.

PROBLEMS TO BE SOLVED BY THE INVENTION

As ultrasound inspection systems, in general, there is an electronic scanning type in addition to a mechanical scanning type. An ultrasound transducer of the electronic scanning type formed by arranging a number of rectangular transducer chips in a row, each transducer chip forming the ultrasound transducer is sequentially actuated so as to be scanned in the arrangement direction of the transducer chips. Such the ultrasound transducer of the electronic type has an advantage as making various wave phases by controlling emission timing of each transducer chip. Japanese Unexamined Patent Application Publication No. 8-52138 discloses an ultrasound endoscope having an ultrasound transducer performing ultrasonic scanning of this type. Aside such the ultrasound endoscope formed in indivisible combination of ultrasonic observing means with endoscopic observing means, an ultrasound inspection apparatus detachable from an endoscope formed so as not to limit the original function as an endoscope, that is the ultrasound probe inserted through the endoscope as disclosed in the foregoing Japanese Unexamined Patent Application Publication No. 11-42231, cannot be constituted as the electronic scanning type. There are such reasons for this fact as that the outer diameter of a flexible cord is limited because it is inserted into a treating instrument guide channel so that a number of wires connected to a number of transducer chips cannot be passed therethrough, and that it is extremely difficult that the ultrasound transducer is steadily held in an assembled state in an endoscope because the ultrasound transducer of the electronic scanning type is extremely larger in size and weight compared with a single-chip transducer.

SUMMARY OF THE INVENTION

In view of the above-mentioned problems, it is an object of the present invention to expand the utility of an endoscope by detachably assembled into an endoscope with an ultrasound inspection apparatus having an electronically scanning ultrasound transducer.

It is another object of the present invention to enable one endoscope to be used for the independent inspection by the endoscope, for the combination of endoscopic inspection and ultrasound inspection, and further for the independent ultrasound inspection as well.

It is another object of the present invention to enable one ultrasound inspection apparatus to be assembled for plural endoscopes to be used.

It is another object of the present invention to enable a puncture instrument led out from a treating instrument outlet portion of an endoscope to be securely brought within a field of ultrasonic observing vision when an ultrasound inspection apparatus having an ultrasound transducer for electronically scanning is detachably connected to the endoscope.

It is another object of the present invention to enable an ultrasound transducer detachably attached to an endoscope to be intimately contacted with a body cavity's wall, etc.

In order to achieve the above-mentioned objects, according to the present invention, there is provided an ultrasound inspection apparatus comprising: an ultrasonic scanning portion having an ultrasound transducer attached thereto in the front end side for performing ultrasonic scanning by arranging transducer chips in an array arrangement; an endoscope-placing portion disposed at a base side position of the ultrasonic scanning portion to be mounted for a distal end portion of an insertion unit of an endoscope; an endoscope-fixing portion for detachably fixing the distal end portion placed on the endoscope-placing portion; and a signal cable formed of wires extending from the base end position of the endoscope-placing portion.

When performing ultrasound inspection, a puncture instrument is generally used in combined therewith. That is, as a result of the ultrasound inspection, for sampling of texture or medical treatment, etc., the puncture instrument should be punctured into a body to be inspected. When the puncture instrument is operated inside a body cavity, the observation with an endoscope is required and the observation by ultrasonic scanning is further needed after it is punctured into the body. An guide channel for inserting treating instruments of the endoscope is always brought into the observing field. When the ultrasound inspection apparatus is assembled to the endoscope, the positional relationship to the ultrasonic scanning portion in the ultrasound inspection apparatus is also important in order to bring the treating instrument within the ultrasound inspection field.

Therefore, a guide portion in a form of a guide groove is preferably disposed between the ultrasonic scanning portion and the endoscope-placing portion to be communicated with a treating instrument guide channel formed in the distal end portion, the guide groove for guiding a treating instrument led out from the treating instrument guide channel toward a scanning region of the ultrasound transducer. More preferably, a guide pipe is disposed between the ultrasonic scanning portion and the endoscope-placing portion, wherein the guide pipe is linked to the treating instrument guide channel of the distal end portion, the guide pipe for guiding a treating instrument led out from the guide channel toward a scanning region of the ultrasound transducer, and the guide pipe formed to be insertable into the guide channel by a predetermined length.

The ultrasonic scanning portion is formed by arranging transducer chips in an array arrangement. When it is assembled to the endoscope, the inspecting field by the endoscope and the leading-out direction of the treating instrument is the axially forward direction. Therefore, it is desirable that the ultrasound inspection field by the ultrasonic scanning portion is located in the obliquely front. For this purpose, a front inclined surface slanting downward toward the tip side may be formed in the front-end portion of the endoscope-placing portion and the ultrasonic scanning portion may be arranged on the front inclined surface. In order to bring the treating instrument led out from the endoscope apart from the transducer chips forming the ultrasonic scanning portion, the transducer chips may be arranged only on the front inclined surface.

The endoscope-fixing portion has a mechanism for fixing the ultrasound inspection apparatus to the distal end portion of the endoscope. As a specific structure thereof, the endoscope-fixing portion may be formed of curved elastic plate pieces arranged with both lateral ends of the endoscope-placing portion, the elastic plate pieces connecting the distal end portion of the endoscope thereto so as to embrace the distal end portion. The endoscope-fixing portion may be formed by an elastic ring, which is a different member from a body unit formed by uniting the ultrasonic scanning portion and the endoscope-placing portion, to be detachably attached to the body unit together with the distal end portion of the endoscope. Further, the endoscope-fixing portion may be formed of a closed loop shaped ring portion arranged with the endoscope-placing portion. When the endoscope-fixing portion is formed of elastic plate pieces or the closed loop shaped ring portion, the endoscope-placing portion may be provided with a extracted portion rising obliquely toward the base end of the endoscope-fixing portion, thereby even if the endoscope-fixing portion is slipped off from the distal end portion of the endoscope, it can be easily recovered from the inside the body cavity because there is not a difference in level on the transitional portion from the endoscope-placing portion to the endoscope-fixing portion.

Then, as a structure of the signal cable, when the signal cable has a flat cross-section and is placed so that the flat plane of the signal cable faces in a direction orthogonal to a one-way curving direction of the angle portion at least in a position along the angle portion, during the curving of the angle portion, the signal cable is curved smoothly following the curving, so that the angle portion cannot be twisted. The signal cable from the endoscope-placing portion may be divided into two bundles so that these bundles may be arranged at substantially symmetrical positions relative to the center line of one direction of curving the angle portion at least in a position along the angle portion, so that the similar function can be obtained. Although the two bundles of the signal cable may be extended as they are, they can be combined into one at a position passing through the angle portion for the simpleness of the routings.

The medical treatment of a diseased portion, etc., is performed in the state that the ultrasound inspection apparatus is attached to the insertion unit by protruding the puncture instrument from the leading-out route for treating instruments so as to puncture into a body. For this purpose, the puncture instrument is required to bring it within the ultrasound inspection field. To this end, ultrasound beams emitted from the ultrasound transducer may be arranged at a position across at least part of a passage of the treating instrument. Also, the ultrasonic scanning portion may be arranged in a position lower than the angle portion while an emitting and receiving surface of the ultrasound transducer may face in a direction orthogonal to the center line of vertically curved the angle portion, so that the puncture instrument is more securely brought within a ultrasound beams emitted from the ultrasound transducer. For this purpose, the endoscope-placing portion may be provided with a portion for positioning the distal end portion of the insertion unit in its circumferential direction.

Furthermore, in accordance with another aspect of the present invention, there is provided an ultrasound inspection apparatus to be detachably connected to an endoscope, the ultrasound inspection apparatus being attached to the endoscope for performing electronic ultrasonic scanning interchangeably with an end cap attached to a distal end portion forming an insertion unit of the endoscope so as to cover the front end face of the distal end portion, the end cap having a nozzle for spraying washing fluid toward an observing window, the ultrasound inspection apparatus comprising: an endoscope connecting mechanism formed of an end cover for covering the front face of the insertion unit and having a nozzle attached to the outer surface thereof, and a peripheral barrel arranged with the end cover for covering the outer peripheral portion of the distal end portion; and an ultrasonic scanning mechanism protruded from the end cover toward the front and having an ultrasound transducer attached thereto for performing ultrasonic scanning by arranging transducer chips in an array arrangement.

In this case, the ultrasonic scanning mechanism may have a planar or convex-curved inclined surface slanting downward from the end cover toward the front, and transducer chips consisting of the ultrasound transducer may be preferably arranged on the inclined surface in the inclining direction. Also, the endoscope connecting mechanism may be provided with fixing means formed on the outer surface of a peripheral barrel thereof for detachably fixing the endoscope connecting mechanism on the outer peripheral surface of the distal end portion of the insertion unit.

These and other objects, constitutions, and effects of the present invention will become more apparent from the following embodiments of the present invention described with reference to the drawings. Of course the present invention is not understood by limiting to the embodiments.

BRIEF DESCRIPTION OF THE DRAWINGS

In the drawings:

FIG. 1 is an entire configuration view of an ultrasound inspection apparatus detachably connected to an endoscope according to a first embodiment of the present invention shown together with the endoscope;

DESCRIPTION OF THE EMBODIMENTS

Figure 2:
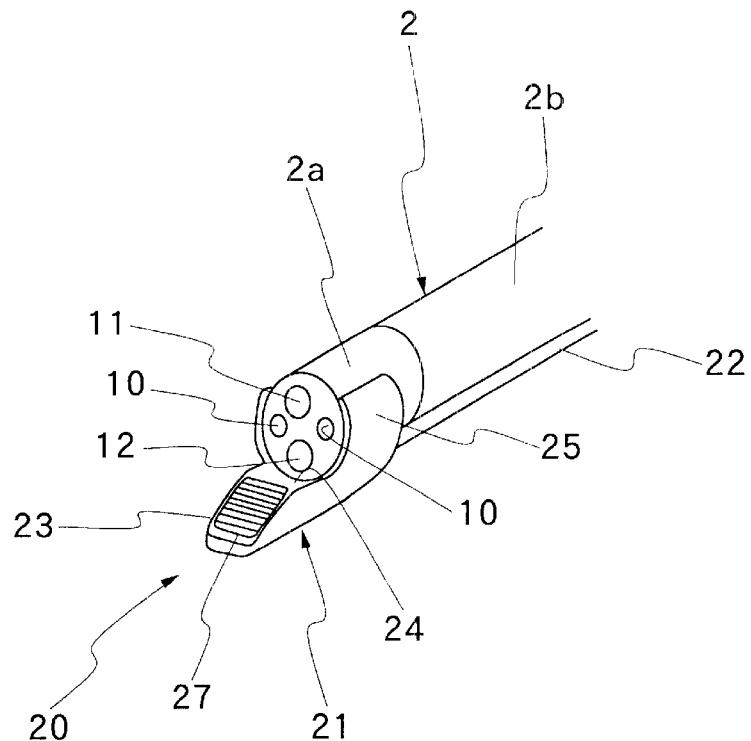
FIG. 2 is an exterior view of an essential part of an ultrasound inspection apparatus showing a connected state of a body thereof to an insertion unit of an endoscope.

Embodiments according to the present invention will be described below based on the drawings. In FIG. 1, reference numeral 1 denotes an endoscope, 20 denotes an ultrasound inspection apparatus, and as shown in FIG. 2, the ultrasound inspection apparatus 20 is detachably assembled to the endoscope 1.

The endoscope 1 is formed of, as is well known, an insertion unit 2, an operation unit 3 arranged in line with the base end of the insertion unit 2, and a universal cord 4 extending from the operation unit 3. A light-source connector 5 and an electrical connector 6 are diverged from the base end of the universal cord 4A. A light-source and a processor are detachably connected to the light-source connector 5 and the electrical connector 6, respectively. In general, the light-source device and the processor are unitarily formed to be a light-source unit 7 having a display of endoscopic images.

The insertion unit 2 comprises, from the fore side, in order, a distal end portion 2a, an angle portion 2b, and a flexible portion 2c. On the front end of the distal end portion 2a, as will be understood from FIG. 2, illuminating windows 10 (two illuminating windows are shown in the drawing; however, there need not necessarily be two windows) and an observing window 11 are formed, and the illuminating windows 10 face an emitting end of a light guide. At an image forming position of an objective lens attached to the observing window 11, a solid-state imager is mounted. Furthermore, a treating instrument outlet opening 12 for leading-out a treating instrument such as a forceps is opened on the front end face. The treating instrument outlet opening 12 is connected to a treating instrument inlet 13 arranged in the operation unit 3 with an guide channel for inserting treating instruments (not shown). The angle portion 2b can be vertically and horizontally curved by operation of an angle knob 14 arranged in the operation unit 3. The flexible portion 2c has a flexible structure to distort in any arbitrary direction along an insertion route.

Figure 3:
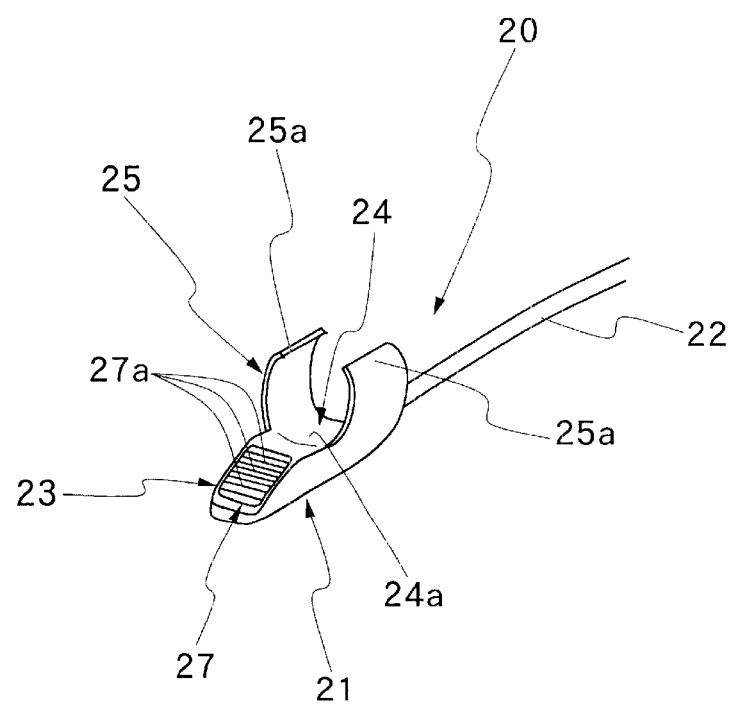
FIG. 3 is an exterior view of the body of the ultrasound inspection apparatus.

The ultrasound inspection apparatus 20 is formed of, as shown in FIG. 2, a main body 21 and a signal cable 22. As is apparent from FIG. 3, the fore end portion of the main body 21 is an ultrasonic scanning portion 23 having an endoscope-placing portion 24 arranged therewith, and an endoscope-fixing portion 25 is arranged with the endoscope-placing portion 24. The signal cable 22 is extended from the endoscope-placing portion 24 in the main body 21 and the end portion of the signal cable 22 is a connector 22a detachably connected to an ultrasonic observing unit 26.

The front-end portion of the endoscope-placing portion 24 has a protruded portion having a shape obliquely downwardly inclined toward the front. This protruded portion is the ultrasonic scanning portion 23. On the plane obliquely inclined toward the front in the ultrasonic scanning portion 23, an ultrasound transducer 27 is placed. The ultrasound transducer 27 is formed by arranging a number of rectangular transducer chips 27a in line, so that electronic scanning is performed by sequentially actuating these transducer chips 27a. Therefore, the ultrasound transducer 27 shown in the drawing is suitable for performing electronic linear scanning (or convex scanning). The entire outer shape of the ultrasonic scanning portion 23 having the ultrasound transducer 27 placed thereon is rounded without edges or sharp points.

The endoscope-placing portion 24 formed in the base side of the ultrasonic scanning portion 23 has a predetermined thickness and comprises a placing surface 24a, which has an arc-circular surface agreeing with the radius of curvature of the outer face of the distal end portion 2a in the insertion unit 2 of the endoscope 1, and an inside portion being formed a passage for signal wires connected to each transducer chip 27a of the ultrasound transducer 27. These wires are bundled to be inserted through the signal cable 22 connected to the endoscope-placing portion 24.

The endoscope-fixing portion 25 is formed of a right and left pair of elastic plate pieces 25a and 25a embracing the distal end portion 2a. The endoscope-fixing portion 25 is unitarily arranged with the endoscope-placing portion 24 and is formed so that the elastic plate pieces 25a and 25a extend to be curved from both sides. The elastic plate pieces 25a forming the endoscope-fixing portion 25 abut the outer face of the distal end portion 2a in the insertion unit 2 while the placing surface 24a in the endoscope-placing portion 24 also abuts the outer face of the distal end portion 2a. The distal end portion 2a of the main body 21 in the ultrasound inspection apparatus 20 is generally covered therewith at an angle of 180° or more, preferably substantially 270°. The inner surfaces of both the elastic plate pieces 25a are curved, and especially in the vicinity of connecting portions to the endoscope-placing portion 24, have an arc-circular shaped curvature substantially agreeing with that of the outer face of the distal end portion 2a, and at least the tip portion of these surfaces has a smaller radius of curvature than that of the distal end portion 2a. Therefore, a force pushing the distal end portion 2a toward the endoscope-placing portion 24 is exerted by the tip portion of both the elastic plate pieces 25a. Consequently, the main body 21 of the ultrasound inspection apparatus 20 is detachably connected to the endoscope 1, and is held and not separated therefrom in the connected state.

The signal cable 22 starting from the endoscope-placing portion 24 extends along the insertion unit 2 of the endoscope 1. Since the main body 21 of the ultrasound inspection apparatus 20 is connected to the distal end portion 2a of the insertion unit 2, when the insertion unit 2 is inserted into a paintient's body, the ultrasound inspection apparatus 20 is also inserted thereinto following the insertion unit 2. Since the insertion unit 2 is relatively long and the insertion unit 2 and the signal cable 22 are flexible, the inserting operation may be occasionally difficult when the signal cable 22 is in a free state. Therefore, it is preferable that the signal cable 22 is fastened to the surface of the insertion unit 2 with connecting members such as elastic rings at several positions, or otherwise the signal cable 22 being formed of a flexible tube in order to insert the insertion unit 2. In the ultrasound inspection apparatus 20, even if the main body 21 is slipped off from the insertion unit 2, it can be recovered from the inside of a body cavity independently of the endoscope by pulling of the base end portion of the signal cable 22.

Figure 4:
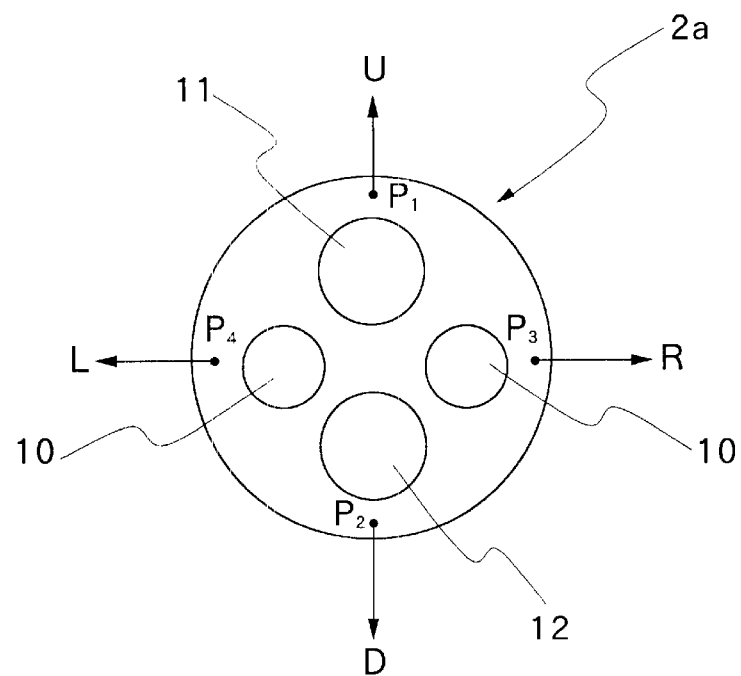
FIG. 4 is a schematic representation of a front end-face in an insertion unit of an endoscope.

The reason why the angle portion 2b can be curved by a remote control from the operation unit 3 is to orient the observing window 11 of an endoscopic observing mechanism to the desired direction. In the endoscope 1 shown in the drawing, the angle portion 2b of the insertion unit 2 can generally be bent in the vertical and horizontal directions. That is, in FIG. 4, operation wires are respectively arranged in positions indicated by P1, P2, P3, and P4; when the operational wire at the position P1 is pulled while the operation wire at the position P2 is pushed, the angle portion 2b is curved in the direction indicated by arrow U, i.e., the upward direction, and when the opposite operation is performed, the angle portion 2b is curved in the direction indicated by arrow D, i.e., the downward direction. Also, when one of the wires positioned at P3 and P4 is pulled while the other is pushed, the angle portion 2b is curved in the direction indicated by arrow R (toward the right) and in the direction indicated by arrow L (toward the left), respectively.

Figure 5:
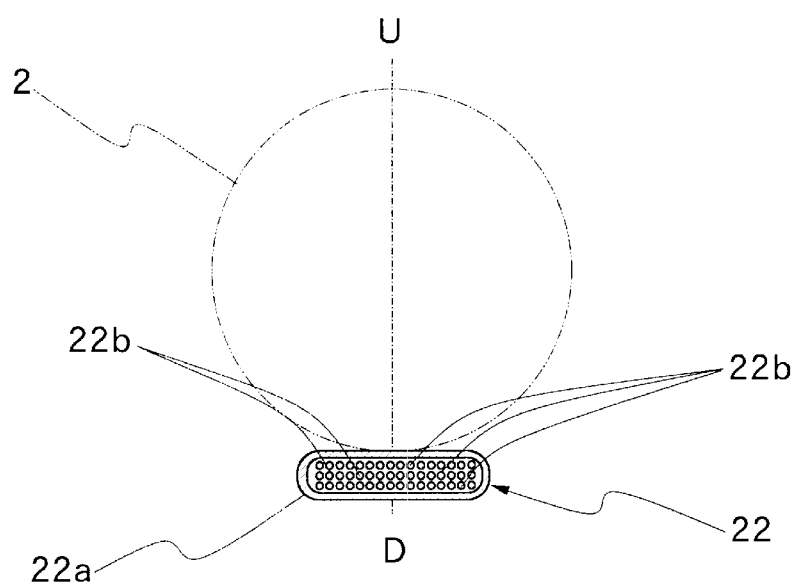
FIG. 5 is a cross-sectional view of a signal cable.

Therefore, as shown in FIG. 5, the line connecting the line U and the line D is the centerline to be curved in the vertical direction. The signal cable 22 is formed by inserting a number of coaxial wires 22b inside a flexible tube 22a therethrough. The cross-sectional shape of the flexible tube 22a may be circular, but it is preferably to form a flat shape, as shown in FIG. 5. The signal cable 22 can be easily curved in a direction in which the flat faces are at the top and the bottom. For this purpose, the center of the flat face of the signal cable 22 is to substantially agree with the line U-D. Moreover, when the signal cable 22 is curved along with the curving of the angle portion 2b, the signal cable 22 is pushed to the surface of the angle portion 2b. Thereby, during the operation of the angle knob 14, the signal cable 22 is to be curved smoothly following the operation, so that the angle portion 2b cannot be twisted.

By so constructing, when the endoscope 1 is independently used, the ultrasound inspection apparatus 20 is disassembled from the endoscope 1. By inserting the insertion unit 2 of the endoscope 1 into a body cavity, illumination is performed from the illuminating window 10 so that the inside of the body cavity can be observed from the observing window 11. As the result of the endoscopic inspection performed as above, when there is a portion to be treated or when a tissue in a body cavity is required to be picked, a required treatment can be performed by protruding an appropriate treating instrument from the treating instrument outlet opening 12. The endoscope 1 has a view in the straight direction as it is without limiting the function of an endoscope, and the diameter of the insertion unit 2 can be thereby reduced, resulting in improved operability in inserting into a body cavity and reduction in a pain of the paitient to be inspected.

On the other hand, when the endoscopic inspection and the ultrasound inspection are combined, or only the ultrasound inspection is performed, the ultrasound inspection apparatus 20 is assembled with the endoscope 1. In the assembling of the ultrasound inspection apparatus 20 in the endoscope 1, by expanding the elastic plate pieces 25a and 25a forming the endoscope-placing portion 24 of the main body 21, the distal end portion 2a of the insertion unit 2 can be brought into abutting engagement with the placing surface 24a on the endoscope-placing portion 24. By abutting the elastic plate pieces 25a and 25a of the endoscope-fixing portion 25 to the outer surface of the distal end portion 2a, the main body 21 of the ultrasound inspection apparatus 20 is fixed in the connected state to the insertion unit 2 due to an elastic force of the elastic plate pieces 25a. Furthermore, if required, the several intermediate positions of the signal cable 22 may be fastened to the insertion unit 2 with elastic rings, etc. The connector 22a arranged in the end of the signal cable 22 is also connected to an ultrasonic observing apparatus 26. Various endoscopes can be detachably assembled in the ultrasound inspection apparatus 20 may be of any type as long as the outer diameter of the distal end portion in the insertion unit is substantially the same.

Upon the ultrasound inspection apparatus 20 is assembled in the endoscope 1, the insertion unit 2 and the main body 21 of the ultrasound inspection apparatus 20 placed in the front end of the insertion unit 2 are inserted into a body cavity upon the observation of inside the body cavity from the observing window 11 in the endoscope 1. Since the main body 21 of the ultrasound inspection apparatus 20 is connected to the insertion unit 2, the diameter of the portion where the main body 21 is attached becomes slightly larger. The ultrasonic scanning portion 23 forming the main body 21 of the ultrasound inspection apparatus 20 is protruded ahead the front end of the insertion unit 2 of the endoscope 1, and the ultrasonic scanning portion 23 has an inclined surface structure in which the thickness thereof continuously decreases toward the front end. Therefore, since the ultrasonic scanning portion 23 is inserted so as to push and extend a narrow portion with the front end thereof, there may be a case that the insertion is rather smoother from the point of passing through of the narrow portion in comparison with the case that the insertion unit 2 of the endoscope 1 having a planar end face orthogonal to the axis is independently inserted. After the main body 21 of the ultrasound inspection apparatus 20 has passed through the narrow portion, there are only the insertion unit 2 and the signal cable 22 inside the narrow portion, so that a physical burden to the paitient is not so much increased.

When the front end of the insertion unit 2 is led to the inside of an inner organ or a coeliac tract to be performed ultrasonic diagnostic, a position to be inspected by ultrasonic waves is confirmed under observation with the endoscope 1. In this connection, the position to be inspected by ultrasound is known in diagnostic in advance or is discovered during the inspection of the inside of body cavities with the endoscope 1 having the ultrasound inspection apparatus 20 assembled thereto. Since the main body 21 of the ultrasound inspection apparatus 20 is arranged to be protruded ahead the distal end portion 2a of the insertion unit 2, an inspecting field from the observing window 11 disposed in the distal end portion 2a is slightly excluded by the main body 21. However, by curving operation of the angle portion 2b arranged with the distal end portion 2a in an appropriate direction, almost the entire portion of the interior organ or the coeliac tract can be brought into the field of vision.

When the ultrasonic scanning portion 23 faces the position to be diagnosed by ultrasonic mechanism in the specific position is inspected with the ultrasound transducer 27. At this time, a coupling medium is filled with between the ultrasound transducer 27 and a coeliac inner wall, or the ultrasound transducer 27 is intimately contacted with the coeliac inner wall. This operation can be performed by operation to curve the angle portion 2b of the endoscope 1. The ultrasound transducer 27 is for performing electronic scanning having an advantage such as making various wave surfaces by controlling emission timing of each transducer chip, resulting in improving accuracy in ultrasound inspection.

When the portion required to be treated with a treating instrument is discovered as a result of the ultrasound inspection, a puncture instrument is led out from the treating instrument outlet opening 12 to puncture from the coeliac inner wall. When the puncture instrument is protruded from the treating instrument outlet opening 12 before puncturing the body, the position of the puncture instrument can be confirmed under observation of the endoscope through the observing window 11. When the puncturing into the body is started, the punctured position is brought into the ultrasonic inspecting field. Therefore, the puncturing operation can be easily performed by confirming the tip of the puncture instrument, so that the tip of the puncture instrument can be smoothly, rapidly, and moreover precisely led to the position to be treated.

In such a manner, when the puncture instrument is used, the ultrasonic inspecting field must be covered by the advanced direction of the puncture instrument completely. However, the base side thereof is not necessarily covered by the ultrasonic inspecting field. Therefore, arranging each transducer chip 27a forming the ultrasound transducer 27 only on the front side inclined surface of the ultrasonic scanning portion 23 prevents the transducer chips 27a forming the ultrasound transducer 27 from coming in touch with the puncture instrument, thus enabling the ultrasound transducer 27 to be protected.

Figure 6:
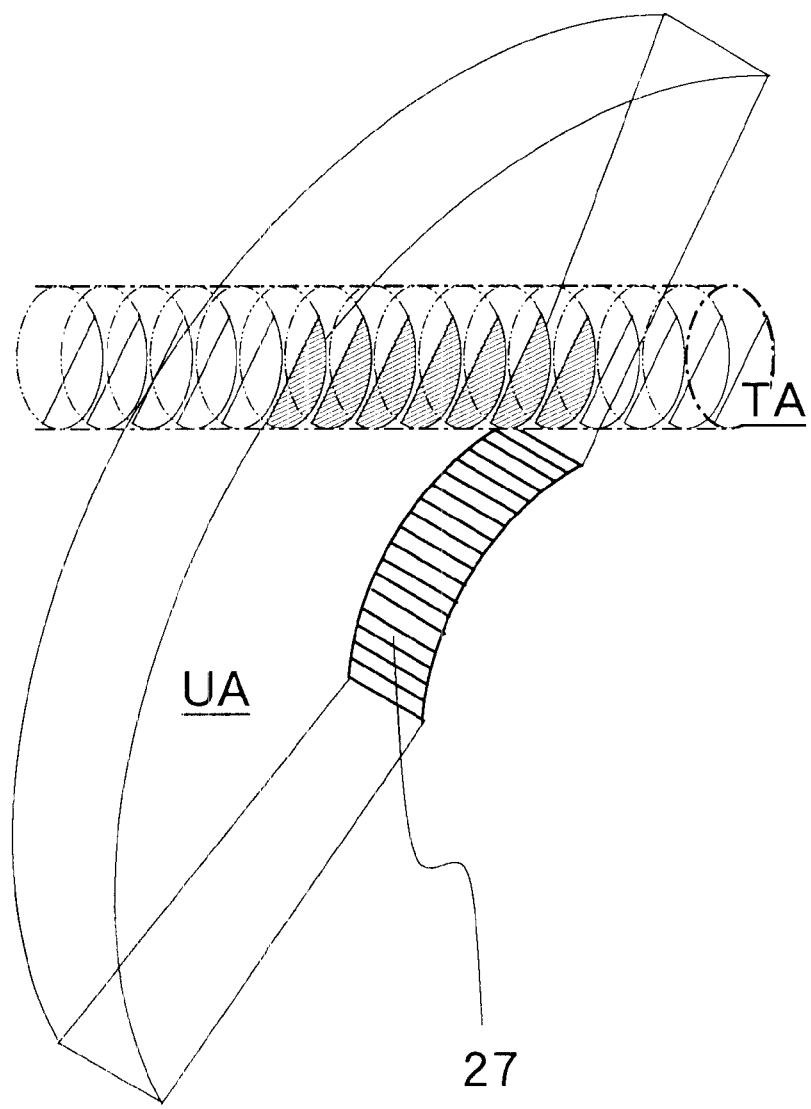
FIG. 6 is a schematic representation showing the relationship between an ultrasonic scanning range and a leading-out direction of a puncture instrument.
Figure 7:
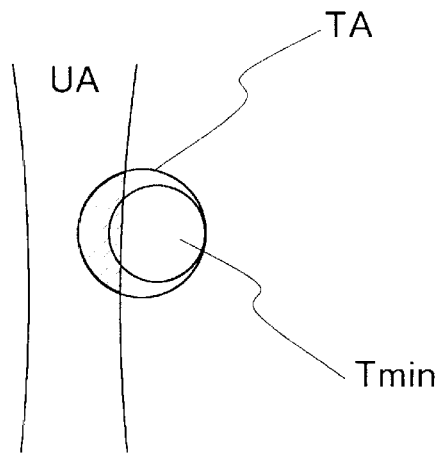
FIG. 7 is a schematic representation showing the overlapped region of the ultrasonic scanning range and the leading-out path of the puncture instrument shown in FIG. 6.

On the other hand, when the puncture instrument is inserted into a body, in order to lead it precisely toward the diseased portion, etc., the tip position of the puncture instrument must be located within the ultrasonic inspecting field by the ultrasound transducer 27. Ultrasound emitted from the ultrasound transducer 27 has a certain width in a direction orthogonal to the scanning direction. This width is a thickness of ultrasound and the puncture instrument led out from the treating instrument outlet opening 12 must be located at least within the range of the thickness of ultrasound. In FIGS. 6 and 7, a region UA bounded by solid lines represents a transmitted region of ultrasonic waves from the ultrasound transducer 27, and a region TA bounded by phantom line denotes extension line of the treating instrument outlet opening 12, i.e., an advanced region of the puncture instrument. Preferably, the region TA overlaps the region UA completely. However, when the thickness of ultrasound from the ultrasound transducer 27 is excessively increased for this purpose, it is not desirable because of reducing resolution in ultrasonic tomographic images. Therefore, at least part of the region TA is set to overlap the region UA. In this case, in order to control the width of the thickness sound field in the ultrasound transducer 27, an acoustic lens is provided thereon and a curvature of the acoustic lens may be appropriately set.

The outer diameter of the puncture instrument used during the ultrasound inspection is not fixed. Therefore, even in the puncture instrument having the minimum diameter indicated by $T_{min}$ in FIG. 7 among the puncture instruments used normally, it must be set to certainly overlap the region UA of the thickness of ultrasound from the ultrasound transducer 27. Thereby, the puncture instrument can be securely led to a target such as the diseased portion after being punctured into a body.

As described above, the endoscope 1 can be independently used during the endoscopic inspection only by detaching the ultrasound inspection apparatus 20 therefrom, and during the combination of endoscopic inspection and ultrasound inspection, the endoscope 1 can be diverted to an ultrasound endoscope by only attaching the endoscope-fixing portion 25 of the ultrasound inspection apparatus 20 to the distal end portion 2a of the insertion unit 2.

Figure 8:
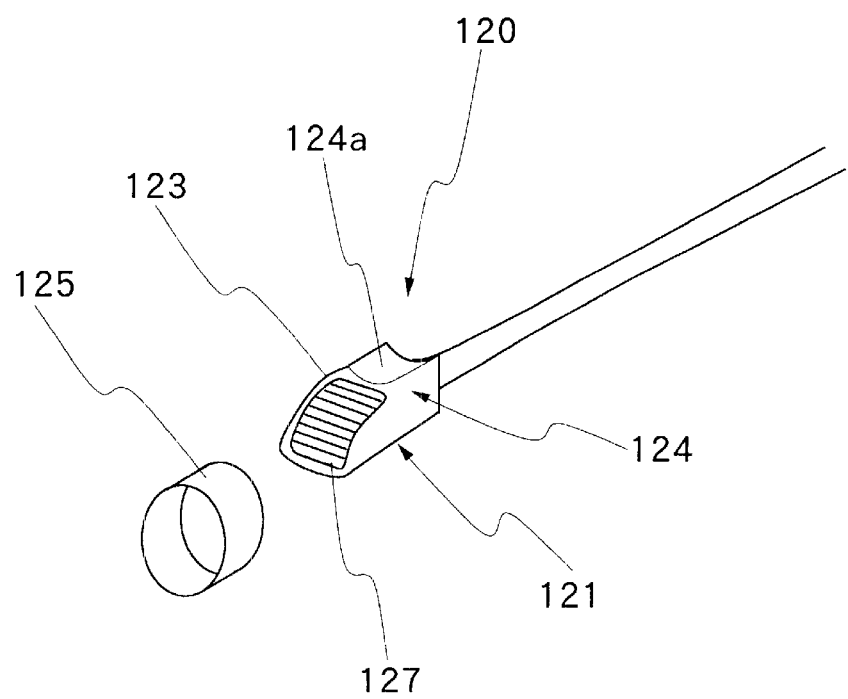
FIG. 8 is an exterior view of an essential part of an ultrasound inspection apparatus of a detachably attaching type to an endoscope according to a second embodiment of the present invention.

The ultrasound inspection apparatus 20 can be attached not only to a specific endoscope but also to any type of endoscope as long as it has a distal end portion capable of being fixed to the endoscope-fixing portion 25. Accordingly, the ultrasound inspection apparatus 20 can be assembled for different endoscopes. The adaptability in the fixing structure to an endoscope with the endoscope-fixing portion helps further more kinds of endoscope to be used. For example, as shown in FIG. 8, an endoscope-fixing portion forming a main body 121 of an ultrasound inspection apparatus 120 may also be an elastic ring 125 having a predetermined width made of a rubber. In this case, a placing surface 124a in an endoscope-placing portion 124 is formed as an arc-circular surface, its radius of curvature thereof being slightly larger than that of the distal end portion 2a of the insertion unit 2, so that endoscopes having insertion units with plural outer diameters can be detachably assembled. In addition, in an ultrasonic scanning portion 123 shown in FIG. 8, an ultrasound transducer 127 is placed, in which transducer chips are arranged in an arc-circular surface in the arranging direction in line, so that the ultrasound transducer 127 can perform electronic convex scanning. The diameter of the elastic ring 125 in a free state is to be sufficiently smaller than the outer diameter of the entire assembly of the main body 121 of the ultrasound inspection apparatus 20 and the endoscope in the position of the distal end portion. Thereby, the main body 121 can be securely fixed thereto without dropping off during the operation even when the outer diameter of the distal end portion is slightly different.

There are many occasions of the therapy using a puncture instrument during the ultrasound inspection. Since the puncture instrument is punctured into a body cavity under observation of an ultrasound transducer, when it protrudes from the treating instrument outlet opening 12 in the distal end portion 2a of the insertion unit 2, it is required to be constantly led in a predetermined direction. Moreover, the leading-out direction is required to have a predetermined angle at least directing upward relative to the axial direction of the insertion unit 2 although it depends on the field of vision of the ultrasound transducer. In order to guide for precisely bringing the puncture instrument led out from a treating instrument outlet opening 12 within an ultrasound inspection field, a structure shown in FIG. 9 may be adopted, for example.

In an ultrasound inspection apparatus 220 shown in the drawing, a main body 221 is provided with a guide portion 228 having a predetermined length which is disposed between an ultrasonic scanning portion 223 and an endoscope-placing portion 224 having an endoscope-fixing portion 225 unitarily formed therewith. The guide portion 228 has an inclined surface linking with the placing surface of the endoscope-placing portion 224 and entirely rising from the endoscope-placing portion 224 toward the ultrasonic scanning portion 223. A guide groove 228a for guiding a puncture instrument is formed on the guide portion 228 at a position linking with the treating instrument outlet opening 12 formed on the end face of the distal end portion 2a when the distal end portion 2a of the insertion unit 2 is placed on the placing surface of the endoscope-placing portion 224.

According to the foregoing structure, the puncture instrument led out straight from the treating instrument outlet opening 12 linking with the treating instrument guide channel along the axial direction of the insertion unit 2 is guided by the guide groove 228a of the guide portion 228 in the main body 221 of the ultrasound inspection apparatus 220 before approaching above the ultrasonic scanning portion 223, so that the puncture instrument can be securely caught within the ultrasound inspection field by an ultrasound transducer 227 provided in the ultrasonic scanning portion 223. Therefore, the positional adjustment of the puncture instrument, etc., is not required, resulting in improved operability. Since the leading-out state of the puncture instrument can be securely detected by the endoscope 1, the operability such as shooting by the puncture instrument is improved.

Figure 10:
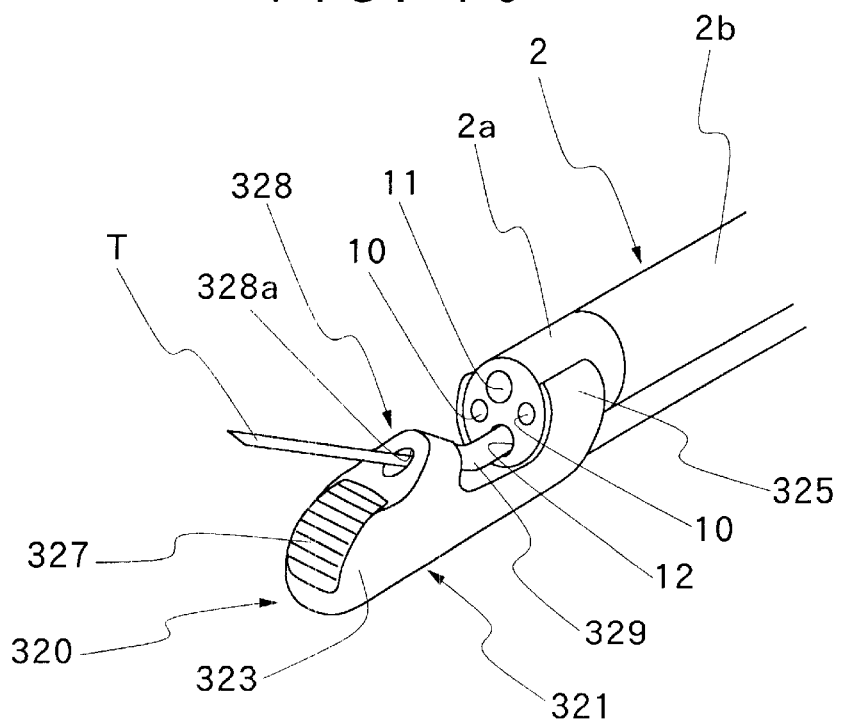
FIG. 10 is an exterior view of an essential part of an ultrasound inspection apparatus according to a fourth embodiment of the present invention showing a connected state of a body thereof to an insertion unit of an endoscope.
Figure 11:
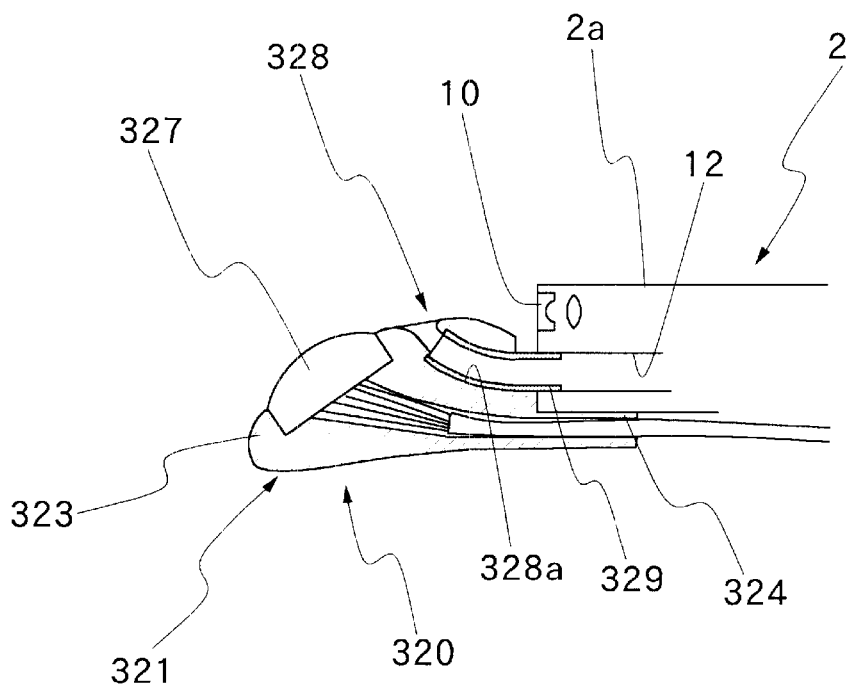
FIG. 11 is a longitudinal sectional view of the essential part of the ultrasound inspection apparatus shown in FIG. 10.

Furthermore, in order to precisely control the relatively positional relationship between a guide portion for guiding the puncture instrument in the ultrasound inspection apparatus side and a treating instrument outlet opening side, a structure shown in FIGS. 10 and 11 may be adopted. In an ultrasound inspection apparatus 320 shown in the drawings, a guide portion 328 for guiding a puncture instrument T is formed between an ultrasonic scanning portion 323 of a body 321 and an endoscope-placing portion 24 protrudes upwardly from the ultrasonic scanning portion 323. A tunnel 328a for passing through the puncture instrument T is formed in the protruding portion of the guide portion 328. The tunnel 328a is connected to a guide pipe 329 and is inclined upwardly at a predetermined angle toward the ultrasonic scanning portion 323. The guide pipe 329 is diverted in the direction to be straight directed by curving a portion thereof having a predetermined length.

By adopting the structure as described above, the main body 321 of the ultrasound inspection apparatus 320 is connected to the distal end portion 2a of the insertion unit 2 so as to insert the end portion of the guide pipe 329 into the treating instrument outlet opening 12 of the endoscope. The ultrasound inspection apparatus 320 is thereby connected fixedly to the endoscope 1. The puncture instrument T inserted from the side of the endoscope 1 can be led out through the guide pipe 329 in the state of being brought into the ultrasonic inspecting field of an ultrasound transducer 327 placed on the ultrasonic scanning portion 323. In this embodiment, an endoscope-fixing portion 325 is unitarily formed with an endoscope-placing portion 224. The contact surface of the endoscope-placing portion 324 to the distal end portion 2a can be enlarged, while the fitting depth of the guide pipe 329 into the treating instrument outlet opening 12 is sufficiently increased, and the guide pipe 329 is tightly fitted into the treating instrument outlet opening 12, therefore the fitting portion of the guide pipe 329 into the treating instrument outlet opening 12 has a function as an endoscope fixing portion.

Figure 9:
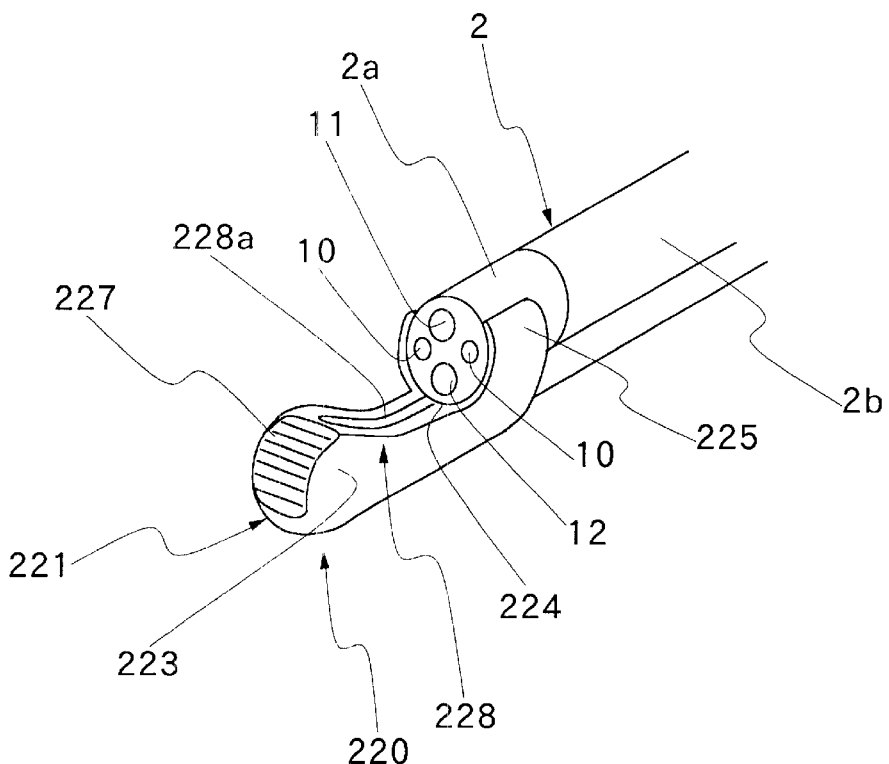
FIG. 9 is an exterior view of an essential part of an ultrasound inspection apparatus according to a third embodiment of the present invention showing a connected state of a body thereof to an insertion unit of an endoscope.

Comparing the third embodiment shown in FIG. 9 with the fourth embodiment shown FIGS. 10 and 11, according to the fourth embodiment, the puncture instrument is completely guided in the channel until being led out from the guide portion 328. Moreover, the channel is directed to the axial direction in the insertion unit 2, and is diverted to the direction of the ultrasonic inspecting field in the guide pipe 329. Therefore, the direction of the puncture instrument can be more precisely controlled. In contrast, as to the third embodiment, although ability in guiding the puncture instrument is slightly inferior than that in the fourth embodiment, there is an advantage that the blinding area of the inspecting field is smaller than that in the fourth embodiment.

Figure 12:
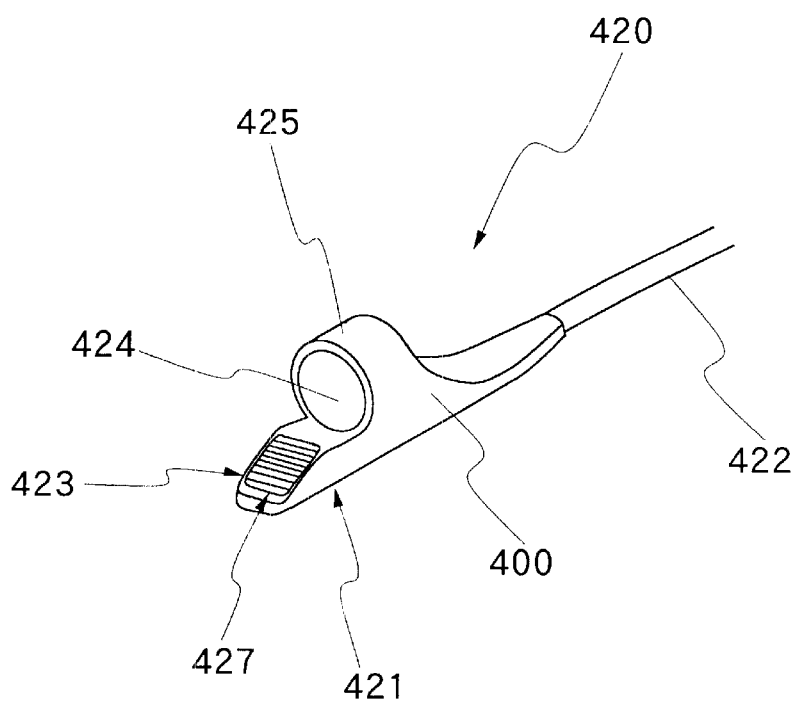
FIG. 12 is an exterior view of a body structure of an ultrasound inspection apparatus according to a fifth embodiment of the present invention.

A fifth embodiment according to the present invention is shown in FIG. 12. A structure in the embodiment is provided with an endoscope-fixing portion 425 shaped like a closed loop and formed from an endoscope-placing portion 424 arranged with an ultrasonic scanning portion 423 having an ultrasound transducer 427 attached thereto in a main body 421 of an ultrasound inspection apparatus 420. A cable exit portion 400 is arranged in the rear portion of the endoscope-placing portion 424, and a signal cable 422 is led out from the cable exit portion 400. The cable exit portion 400 is arranged with the base end of the cylindrical endoscope-fixing portion 425 and has a shape of a circular arc that is substantially semicircular or more wherein an angle of the circular arc continuously decreases from the endoscope-fixing portion 425. Consequently, the transitional portion from the endoscope-fixing portion 425 toward the cable exit portion 400 has a shape having a continuously descending ridgeline. In addition, while at least the ultrasonic scanning portion 423 is made of a hard material, the portions from the endoscope-placing portion 424 to endoscope-fixing portion 425 and the cable exit portion 400 are preferably formed of an elastic member such as a rubber.

In such a manner, the endoscope-fixing portion 425 has a closed loop linking with the endoscope-placing portion 424 and is formed of an elastic member such as a rubber, thereby the distal end portion 2a of the insertion unit 2 can be fixedly connected by inserting it into the endoscope-fixing portion 425. Moreover, even if the main body 421 dropped off from the insertion unit 2, it can be recovered from the inside of a body cavity independently of the endoscope by pulling in the base end portion of the signal cable 422. There is no substantial difference in level on the transitional portion from the endoscope-placing portion 424 of the main body 421 and the endoscope-fixing portion 425 to the signal cable 422, thereby being changed in shape to have a gentle curve, and eliminating a danger that the main body 421 is locked on the way of the route from inside a body cavity. As a result, dangers such as damages in the body cavity and breaking of a wire due to an excessive force applied to the linking portion between the signal cable 422 and the main body 421 can be eliminated.

Figure 13:
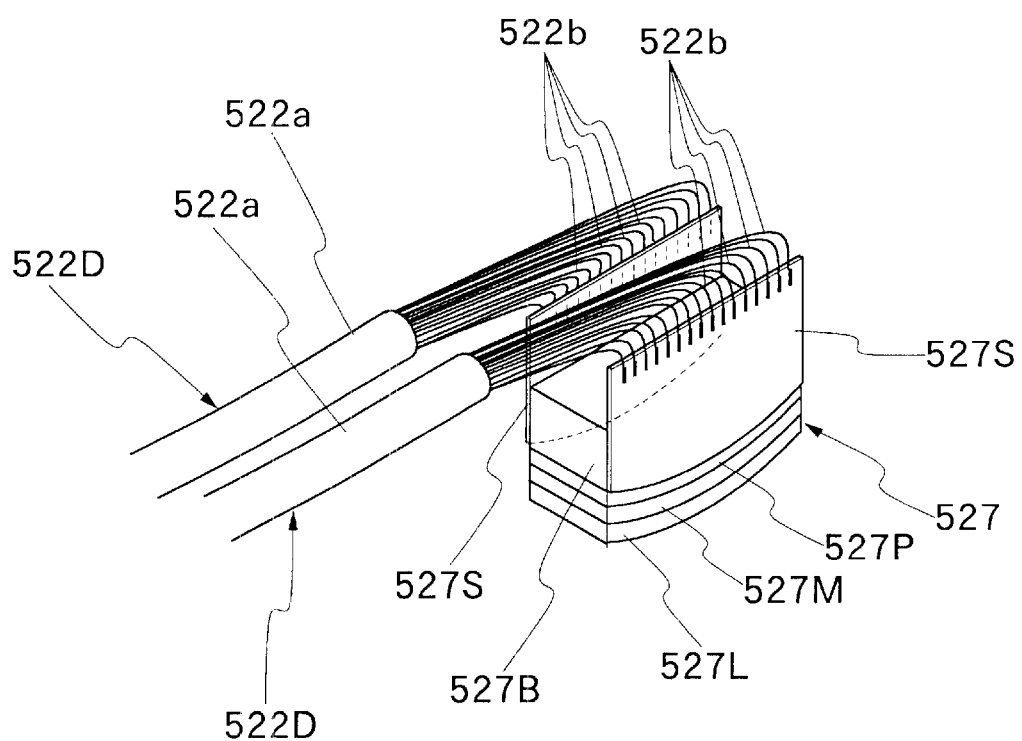
FIG. 13 is a schematic representation showing an ultrasound transducer and signal cables extending from the ultrasound transducer.
Figure 14:
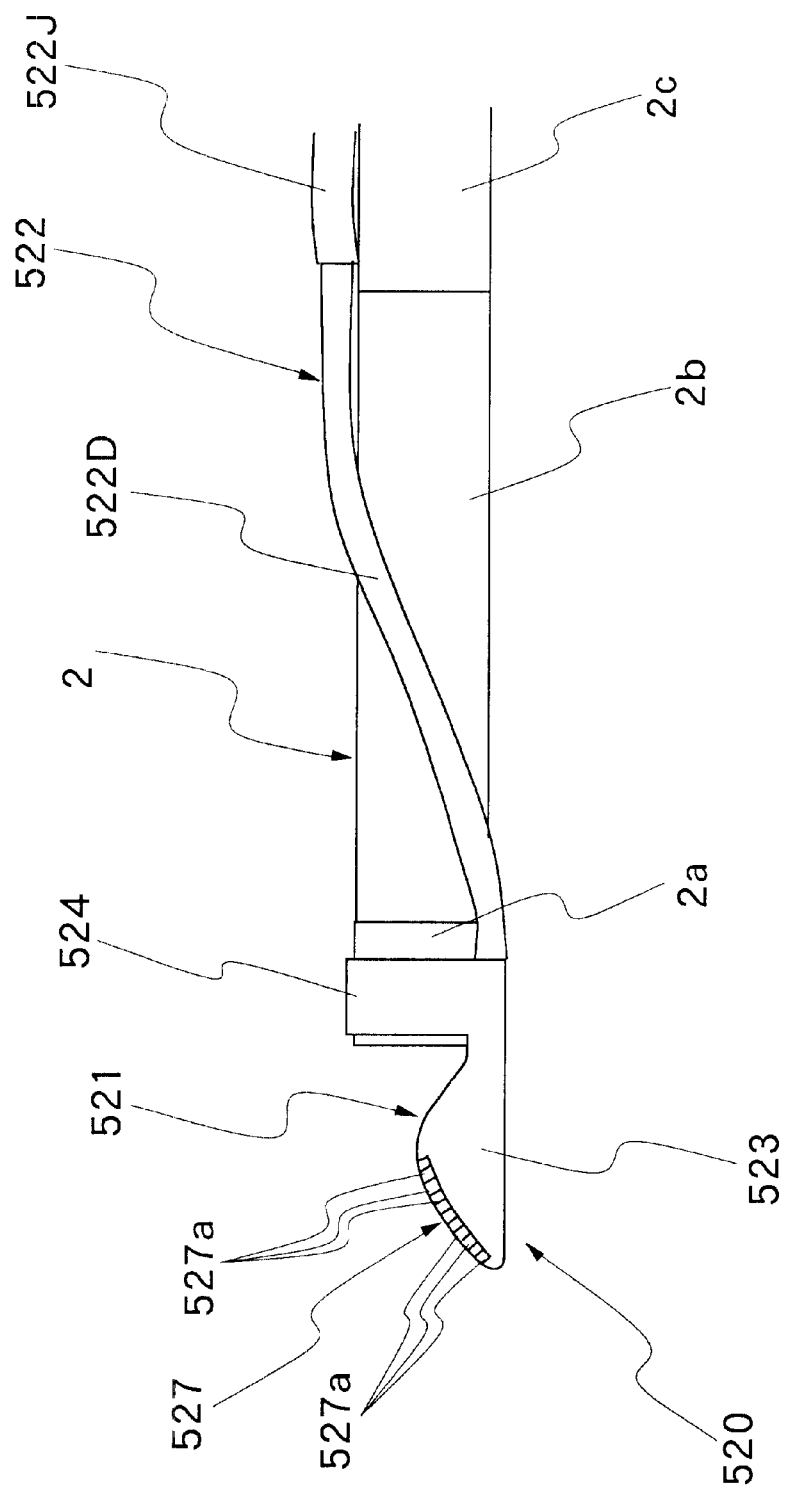
FIG. 14 is a side view showing a routing structure of the signal cables extending from the ultrasound transducer shown in FIG. 13.
Figure 15:
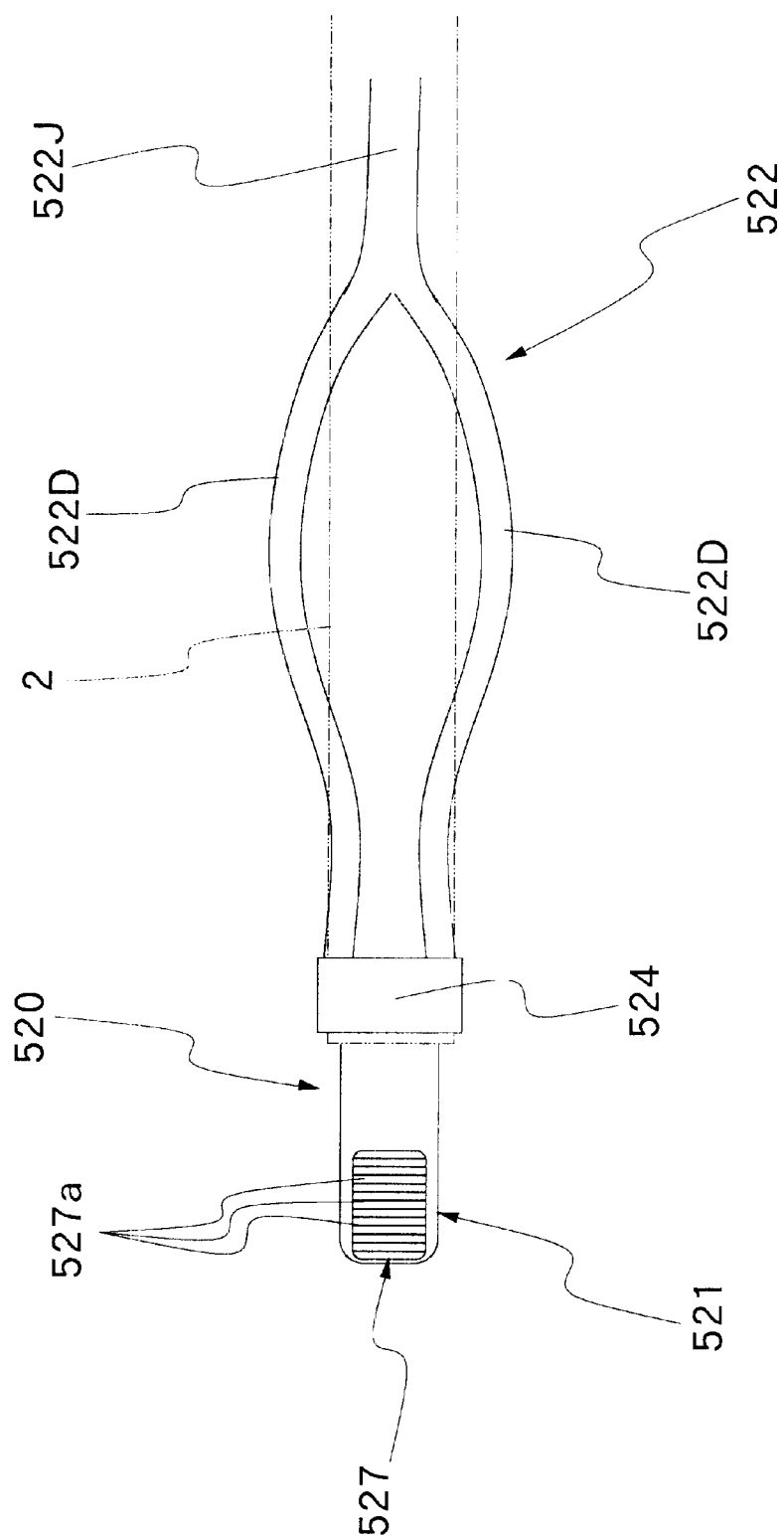
FIG. 15 is a plane view of the routing structure of the signal cables shown in FIG. 14.

Furthermore, an embodiment concerning a routing structure of a signal cable from the ultrasound transducer is shown in FIGS. 13 to 15. As shown in FIG. 13, an ultrasound transducer 527 has a multi-layers consisting of, from the top surface side, an acoustic lens layer 527L, an acoustic matching layer 527M, a piezoelectric element 527P, and a backing member 527B. On both end faces of the backing member 527B at the right and left, flexible substrates 527S and 527S are fastened. A predetermined number of electrodes connected to the piezoelectric element 527P, which is cut into rectangular transducer chips 527a, is provided on both the flexible substrates 527S. Each coaxial wire 522b forming a signal cable 522 is connected to each of these electrodes. Therefore, the respective predetermined numbers of coaxial wires 522b connected to both the flexible substrates 527S are independently bundled into flexible tubes 522a. Consequently, as shown in FIG. 13, two bifurcated cables 522D and 522D extend from an endoscope-connecting portion 524.

These two bifurcated cables 522D and 522D are arranged at bilaterally symmetrical positions relative to the center line of vertical curvature U–D (see FIG. 5) of the angle portion 2b. Therefore, as shown in FIGS. 14 and 15, in the main body 121 of the ultrasound inspection apparatus 120, the two bifurcated cables 522D and 522D are arranged in the lower position in the side of the endoscope-placing portion 124.

However, they are raised upwardly to the base side along the angle portion 2b, and after passed through the angle portion 2b, they are combined into one combined cable 522J at the upper side. That is, as shown in FIG. 15, a closed loop is formed with a body unit 521 of an ultrasound inspection apparatus 520 and the bifurcated cables 522D and 522D extending from the body unit 521 before the combined portion of the combined cable 522J. The insertion unit 2 of the endoscope 1 is passed through the closed loop, so that the distal end portion 2a of the insertion unit 2 is inserted into the endoscope connecting portion 524 of the body unit 521.

By the structure described above, when the angle portion 2b is upwardly curved in order to perform ultrasound inspection with the ultrasound transducer 527, the bifurcated cables 522D and 522D are equally curved without exerting force other than that in the direction U. The signal cable 522D is not curved by the force of the angle portion 2b but is substantially in a free state relative to the angle portion 2b. A resistant force during the angle operation is thereby suppressed to the minimum, resulting in further improved operability. Moreover, although the two bifurcated cables 522D and 522D are in a free state, they are connected into the combined cable 522J in the upper side so as to sit astride the angle portion 2b from the lower side of the angle portion 2b, thereby preventing their disposition.

Figure 16:
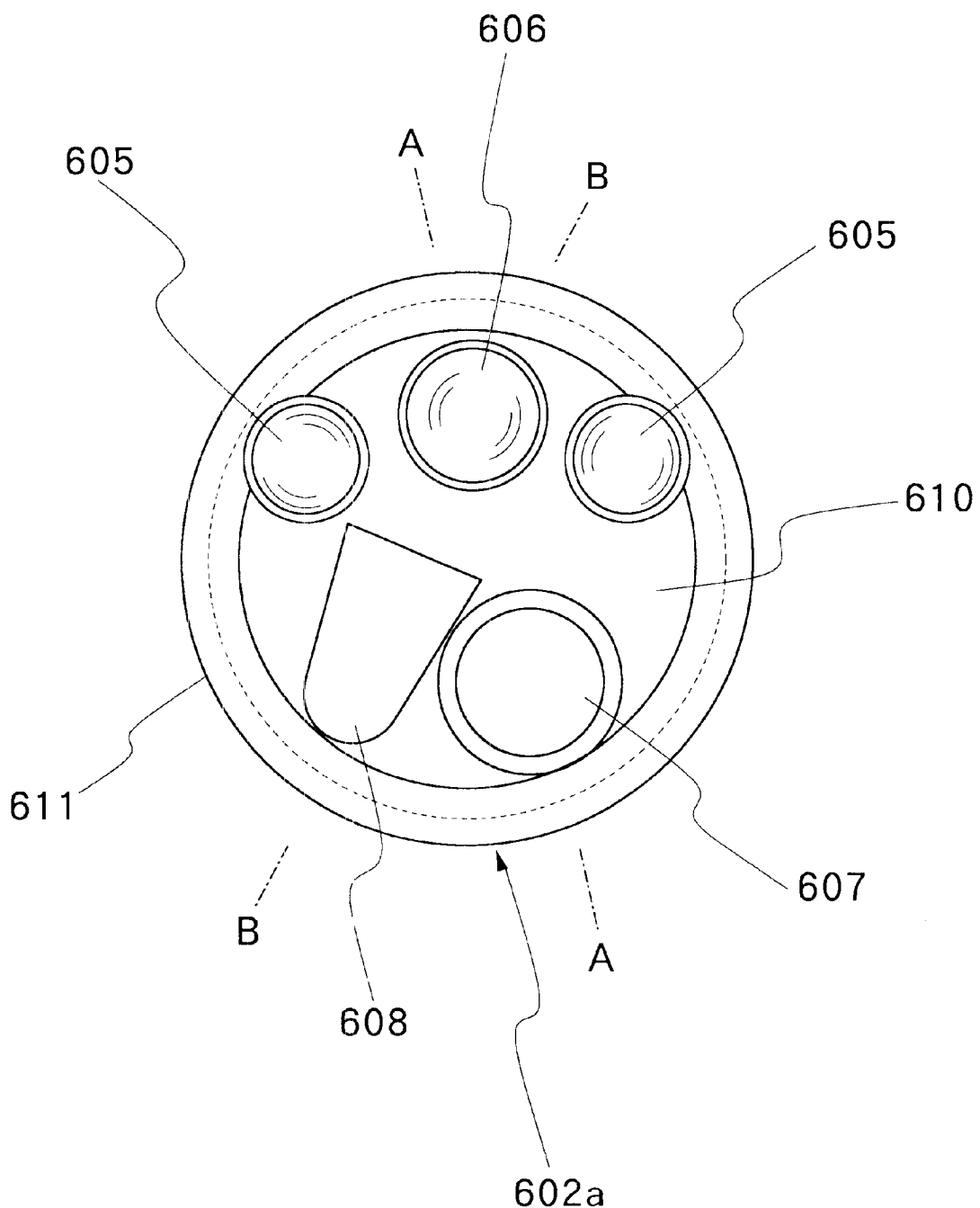
FIG. 16 is an exterior view of a front-end face of an insertion unit of an endoscope to be detachably attached to an ultrasound inspection apparatus according to a sixth embodiment of the present invention.

Further, a sixth embodiment according to the present invention is shown in FIGS. 16 to 22. A structure of a distal end portion 602a of an insertion unit 602 is shown in FIG. 16. On the end face of the distal end portion 602a, an illuminating window 605 and an observing window 606 are provided. An emitting end of a light guide faces the illuminating window 605 and a solid-state imager is placed at an image forming position of an objective lens attached to the observing window 606. Furthermore, a treating instrument outlet opening 607 is opened for leading-out a treating instrument such as a forceps on the end face. A washing nozzle 608 is also placed thereon for spraying a washing liquid and compressed air as a cleaning fluid toward the observing window 606.

Figure 17:
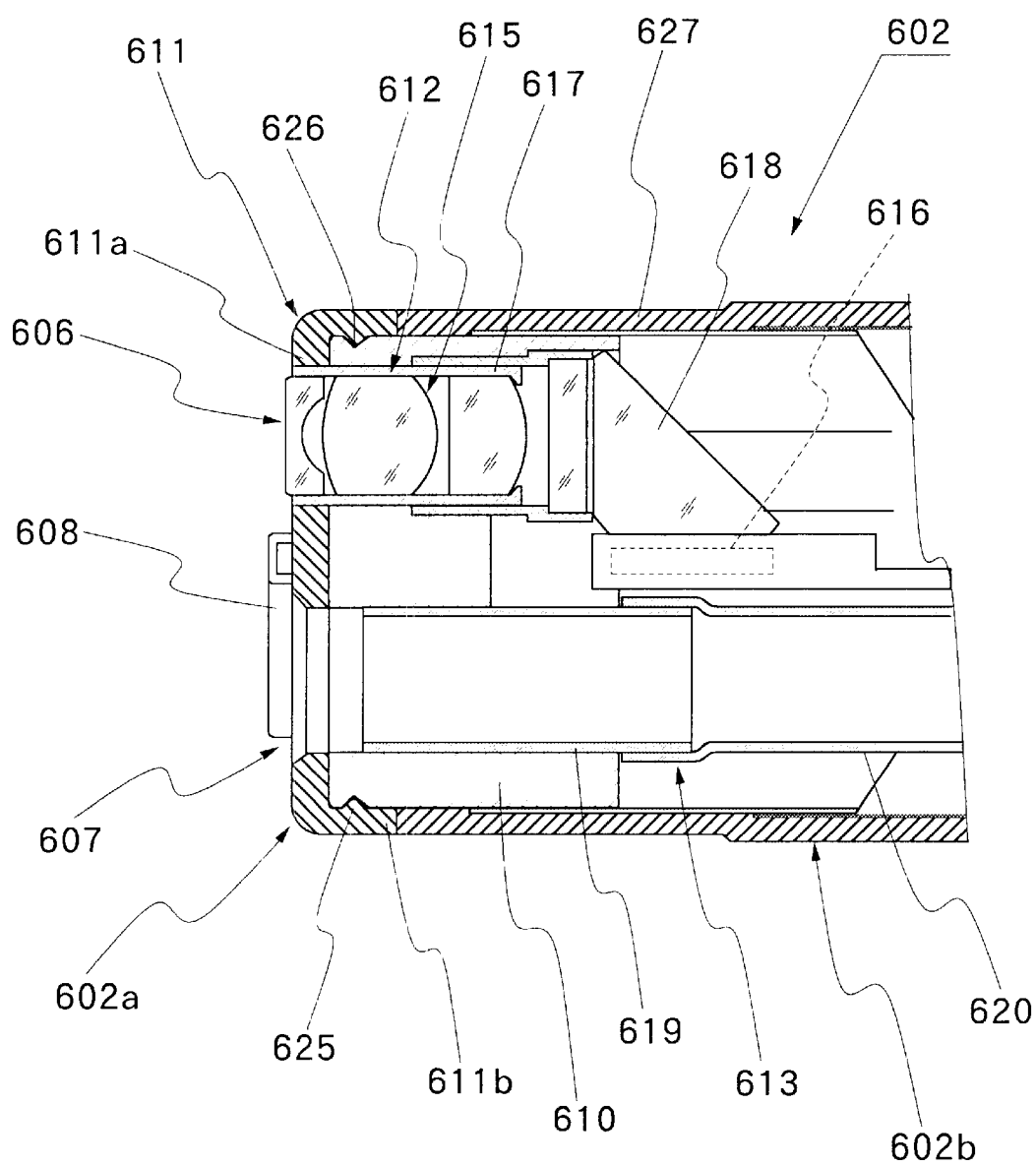
FIG. 17 is a sectional view at the line A—A of FIG. 16.
Figure 18:
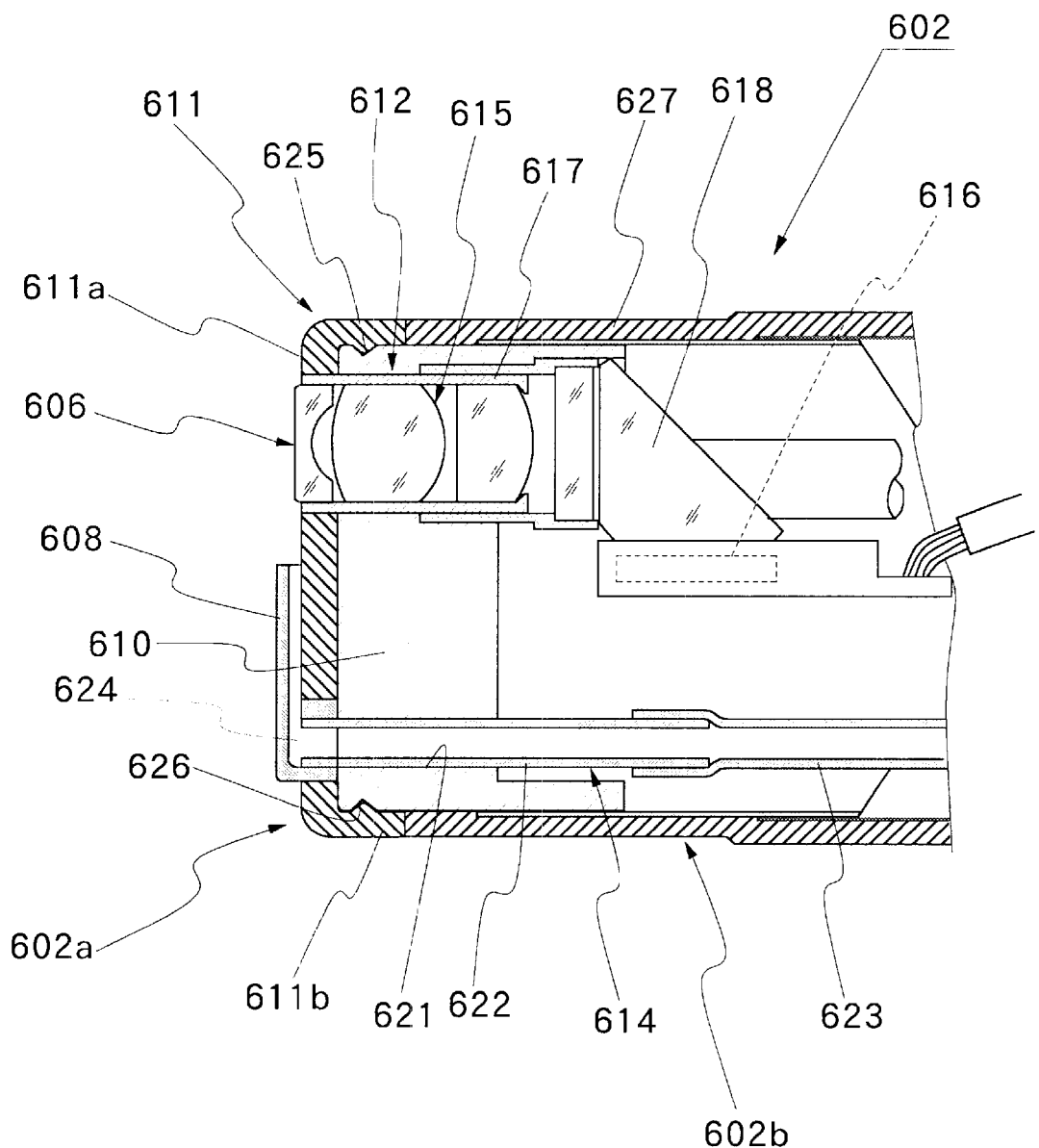
FIG. 18 is a sectional view at the line B—B of FIG. 16.

FIG. 17 shows a sectional view at the line A—A of FIG. 16 and FIG. 18 shows a sectional view at the line B—B of FIG. 16. As will be understood from the drawings, the distal end portion 602a is formed of a main part 610 and an end cap 611 to be detachably connected to the end face of the main part 610. The main part 610 is made of a metal in view of processing, strength and the like, and has through-holes formed for placing the above-mentioned members thereinto. Shown in FIG. 17 are observing means 612 connected to the observing window 606 and treating instrument guiding means 613 connected to the treating instrument outlet opening 607. Also, shown in FIG. 18 are the observing means 612 and fluid supplying means 614 connected to the washing nozzle 608.

The observing means 612 includes an objective optical system 615 and a solid-state imager 616 disposed at the image forming position of the objective optical system 615. Lenses forming the objective optical system 615 are attached within a lens barrel 617 and a prism 618 is attached for bending the optical passage at an angle of 90° in the base end portion of the lens barrel 617. The treating instrument guiding means 613 is formed of a treating instrument inserting pipe 619 attached in the main part 610 and a flexible treating instrument guide channel 620 fitted to the treating instrument inserting pipe 619. Further, the fluid supplying means 614 is formed of a passage 621 bored through the main part 610, a pipe 622 connected to the passage 621, and a tube 623 fitted to the pipe 622.

Every member described above is attached into the through-hole bored in the main part 610 in the axial direction, the washing nozzle 608 has a jet mouth covering the upper portion of the passage 621 and opened toward the observing window 606 in order to direct washing fluid to the observing window 606. When the insertion unit 2 is inserted into a body cavity, there is a possibility that the inner portions of the washing nozzle 608 and the passage 621 are stained with body fluids, etc. Therefore, the washing nozzle 608, the passage 621, further the pipe 622, and the tube 623 must be washed and disinfected every time after use. In order to facilitate the washing and disinfection, the washing nozzle 608 is formed so as to be detachable from the main part 610. The end cap 611 serves to insulate the main part 610 made of a metal and to enable the washing nozzle 608 to be detachable from the main part 610. For this purpose, the washing nozzle 608 is provided in the end cap 611 fixed thereonto. Therefore, a fluid passage 624 is bored through the end cap 611, and through-holes comprising the illuminating window 605, the observing window 606, and the treating instrument outlet opening 607 are formed in the end cap 611. The front-end face of the lens barrel 617 connected to the observing window 606 extends to the front face of the end cap 611. An illuminating lens barrel is connected to the illuminating window 605, and it also extends to the front face of the end cap 611.

The end cap 611 is formed of an end cover 611a for covering the front face of the main part 610 and a peripheral barrel 611b for covering the outer peripheral surface of the main part 610. On the inner surface of the peripheral barrel 611b, an annular retaining rib 625 is formed, while an annular retaining groove 626 to be engaged with the retaining rib 625 is formed on the outer surface of the main part 610. When the end cap 611 is attached to the main part 610, an end face of the peripheral barrel 611b of the end cap 611 abuts an end face of a cover layer 627 of an angle portion 602b so as to prevent a conductive material such as a metal on the outer surface of the insertion unit 602 from being exposed.

By bringing the retaining rib 625 into engagement with the retaining groove 626 for a snapping action, the end cap 611 is connected and fixed to the main part 610. When the retaining rib 625 is disengaged from the retaining groove 626, the end cap 611 can be detached from the main part. Therefore, by detaching the end cap 611 from the main part 610, the washing nozzle 608, the passage 621, the pipe 622, and the tube 623 can be easily and completely washed and disinfected.

Figure 19:
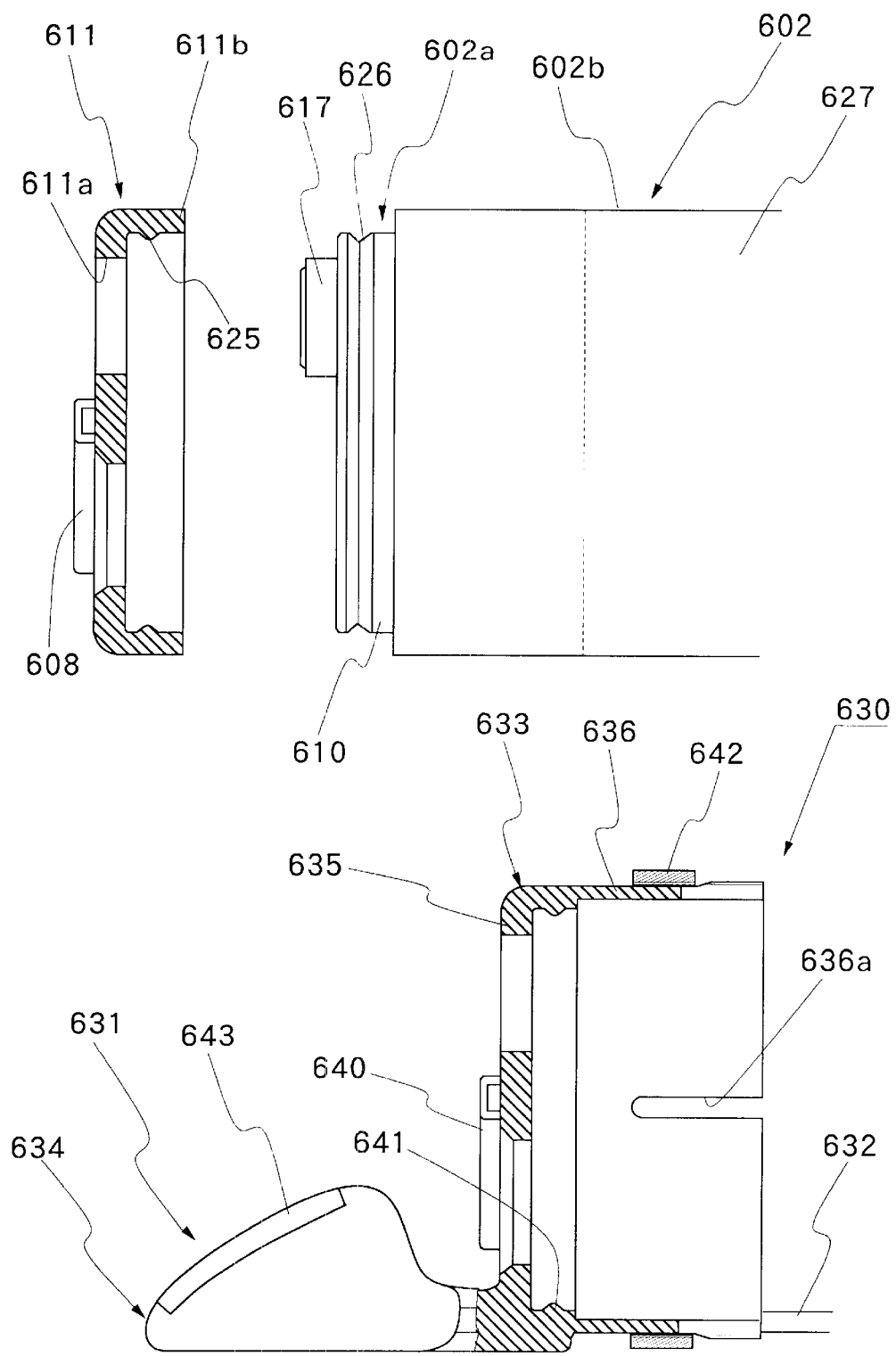
FIG. 19 is a front view of a body unit forming an ultrasound inspection apparatus.
Figure 20:
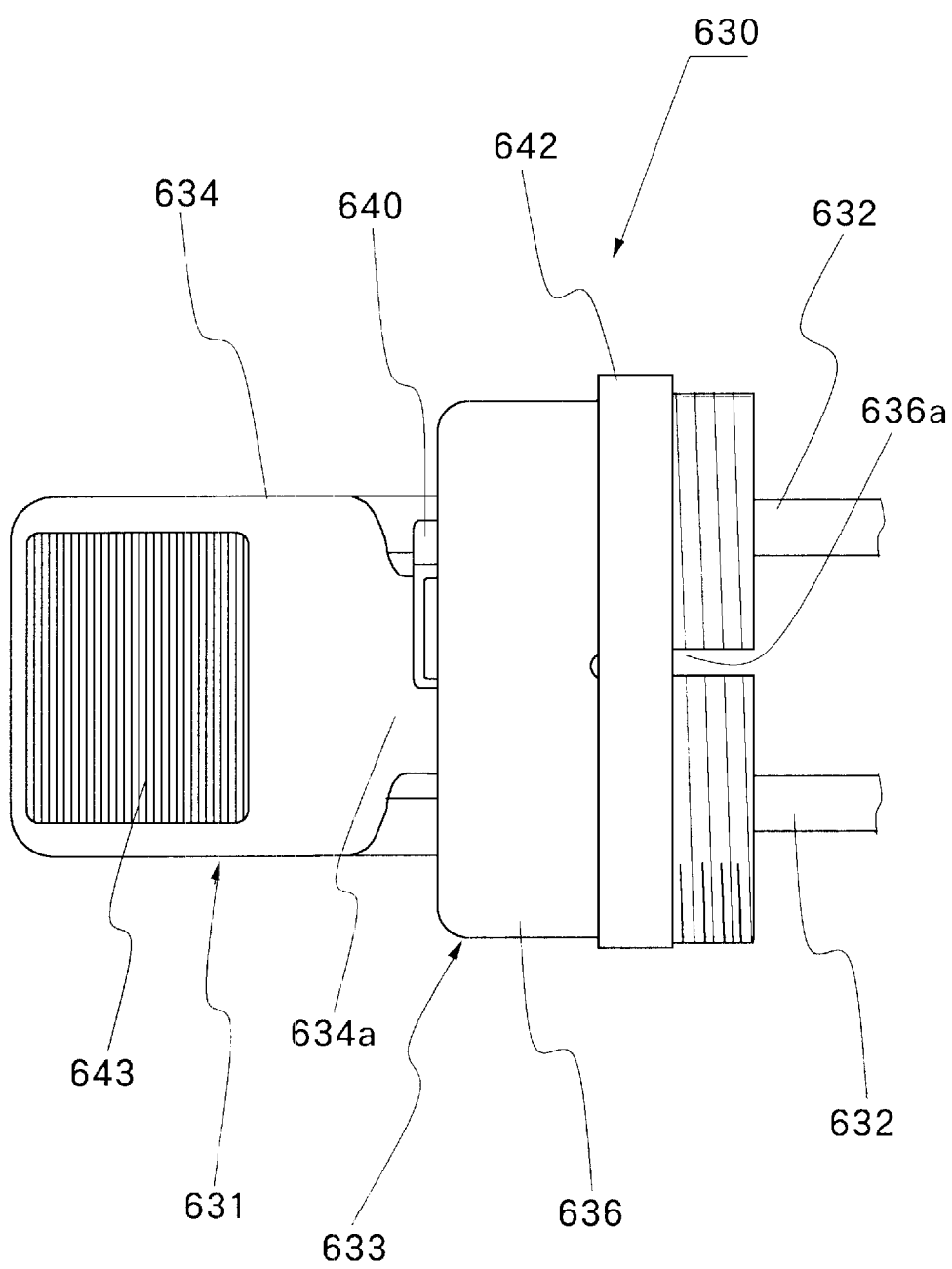
FIG. 20 is a front view of an ultrasound inspection apparatus.

As shown in FIG. 19, to the distal end portion 602a in the insertion unit 602 of the endoscope 601 as assembled in the foregoing manner, a body unit 631 of an ultrasound inspection apparatus 630 can be detachably attached. The ultrasound inspection apparatus 630 comprises the body unit 631 including an ultrasound transducer and a signal cable 632 having a connector at an end thereof to be detachably connected to an ultrasonic observing apparatus. The body unit 631 is attached to the distal end portion 602a in the insertion unit 602 of the endoscope 601, and the signal cable 632 extends along the insertion unit 602. The body unit 631 is coupled to the distal end portion 602a exchanged by the end cap 611 attached to the main part 610. Accordingly, as will be understood from FIGS. 20 and 21, the body unit 631 is formed of an endoscope connecting mechanism 633 to be detachably connected to the distal end portion 602a and an ultrasonic scanning mechanism 634.

The endoscope connecting mechanism 633 is formed of an end cover 635 and a peripheral barrel 636. The end cover 635 has substantially the same structure as of the end cap 611, an illuminating widow 637, an observing widow 638, and a treating instrument outlet opening 639 are opened thereon. A washing nozzle 640 is also provided thereto. On the other hand, different from the end cap 611, the peripheral barrel 636 not only covers the outer peripheral surface of the main part 610 but also extends until a position in that the front portion of the cover layer 627 in the angle portion 602b is thereby covered. On the inner surface of the peripheral barrel 636 in the vicinity of the connecting portion to the end cover 635, a retaining rib 641 is formed so as to be engaged with the retaining groove 626 formed on the outer surface of the main part 610, while on the tip side of the peripheral barrel 636, plural slits having a predetermined length are formed and a threaded portion is formed on the outer surface thereof. In addition, the threaded portion has a slightly larger thickness and outer diameter than those of the other. A screw ring 642 having a threaded inner peripheral face is fitted to the outer peripheral face of the peripheral barrel 636, and when the screw ring 642 is screwed onto the threaded portion of the peripheral barrel 636, the tip end of the peripheral barrel 636 having the slits formed therein is inwardly pressed in the radial direction, so that the peripheral barrel 636 is urged in contact with the cover layer 627. Since the cover layer 627 of the angle portion 602b is formed of an elastic member such as a rubber, when the peripheral barrel 636 is pressed, the cover layer 627 develops a predetermined amount of deflections. The endoscope connecting mechanism 633 has a function to connect and fix the body unit 631 to the insertion unit 602 of the endoscope 601. Extremely steadily fixed state can be obtained by the snapping action engagement between the retaining rib 641 and the retaining groove 626, further the screwing of the screw ring 642.

The ultrasonic scanning mechanism 634 is arranged so as to protrude ahead from the end cover 635, which is part of the endoscope connecting mechanism 633, and to have the substantially planar bottom face and the curved top face thereof. On the top face inclined from the peak toward the front, an ultrasound transducer 643 is placed by arranging a number of rectangular transducer chips across the inclined surface. Wires connected to the ultrasound transducer 643 are divided and inserted into signal cables 632 and 632 connected to both lateral sides of the ultrasonic scanning mechanism 634. For that purpose, in the ultrasonic scanning mechanism 634, the width of a connecting portion 634a to the endoscope connecting mechanism 633 is smaller compared with that of a body portion having the ultrasound transducer 643 placed thereon, and faces are formed on both sides thereof, to which the signal cables 632 are connected.

Due to the structure described above, in the endoscope 601 having the end cap 611 attached to the main part 610 in the distal end portion 602a, when the body unit 631 of the ultrasound inspection apparatus 630 is connected thereto instead of the end cap 611 so as to extend the signal cables 632 across the insertion unit 602, the endoscope 601 performs the function of the ultrasound endoscope.

When assembling the ultrasound inspection apparatus 630 onto the endoscope 601, the end cap 611 is first removed by detaching the retaining rib 625 of the end cap 611 from the retaining groove 626 of the main part 610. Then, the endoscope connecting mechanism 633 in the body unit 631 of the ultrasound inspection apparatus 630 is fitted to the main part 610 so as to engage the retaining rib 641 formed in the peripheral barrel 636 with the retaining groove 626. Next, the body unit 631 is firmly assembled onto the front-end portion of the insertion unit 602 in the endoscope 601 by screwing the screw ring 642 onto the threaded portion of the peripheral barrel 636. Although the ultrasonic scanning mechanism 634 is largely protruded ahead the endoscope connecting mechanism 633, the stability of assembling is steadily maintained.

Figure 21:
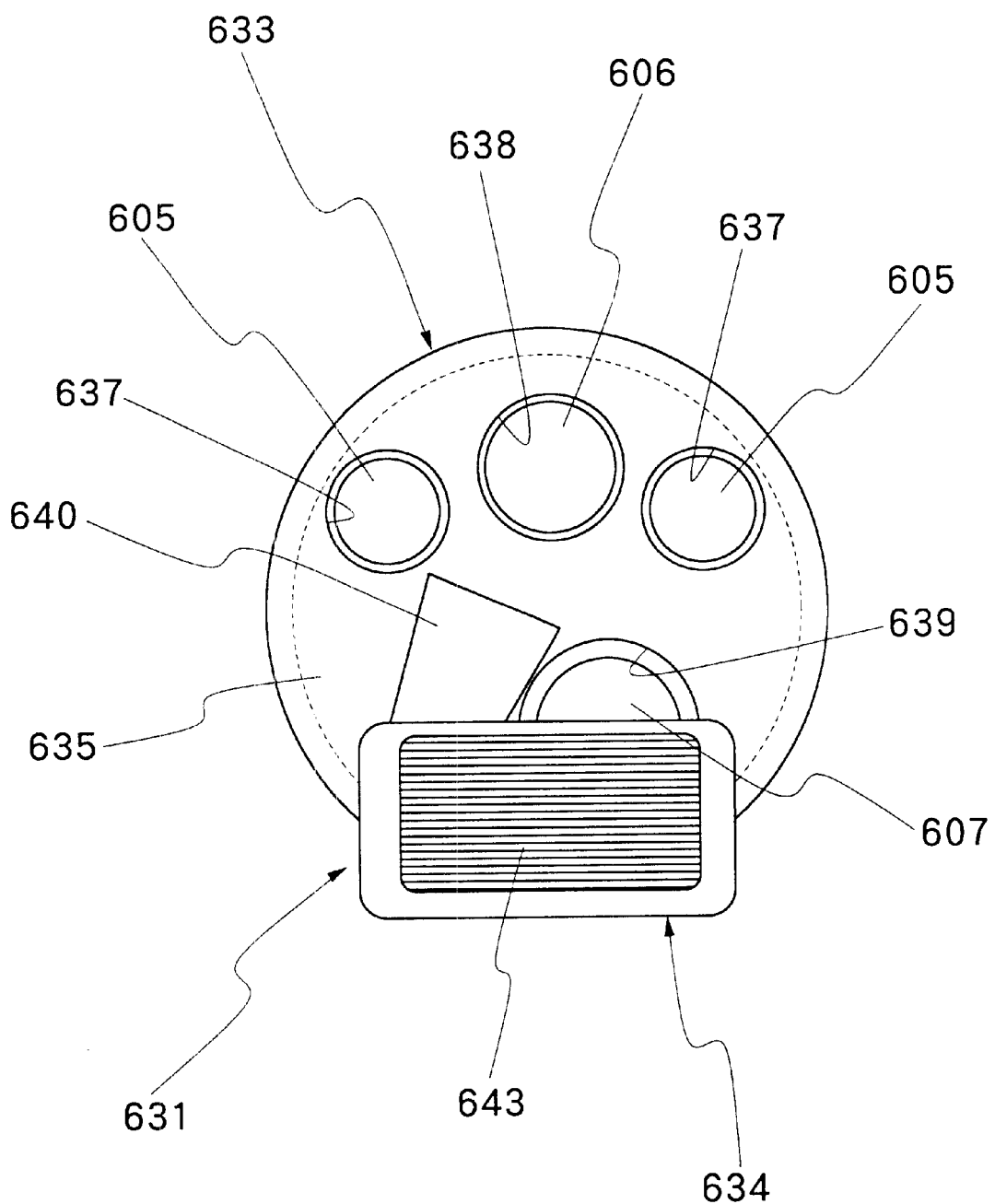
FIG. 21 is a plan view of the ultrasound inspection apparatus shown in FIG. 20.

The position of the ultrasonic scanning mechanism 634 depends on the curving direction of the angle portion 602b of the insertion unit 602 and on the treating instrument guiding means 613. That is, when performing ultrasonic scanning with the ultrasound transducer 643, the ultrasound transducer 643 is abutted on an inner wall of a body cavity, and the angle portion 602b is curved so as to perform this operation. Accordingly, as shown in FIG. 21, the transmitting and receiving surface of the ultrasound transducer 643 is required to face the curving direction of the angle portion 602b, the rising direction thereof, for example.

Figure 22:
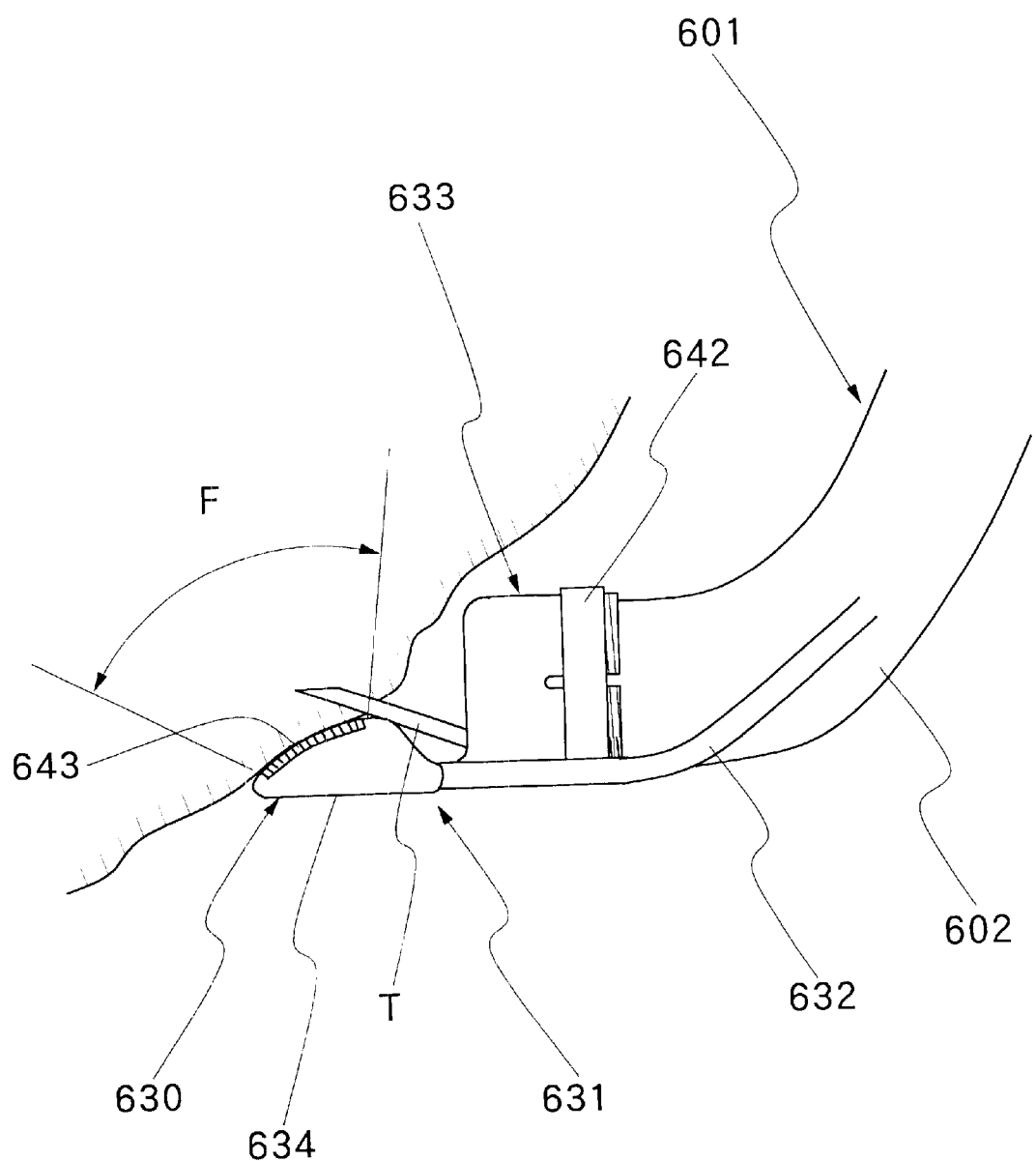
FIG. 22 is a schematic representation showing the function of an ultrasound endoscope formed by assembling an ultrasound inspection apparatus onto an endoscope.

As can be seen from FIG. 22, the puncture instrument T is punctured into a body by being led from the treating instrument outlet opening 639. The position and direction of the puncture instrument T in the body are needed to be within the ultrasonic inspecting field F. In addition, the puncture instrument T is guided by the rising face in the base end of the ultrasonic scanning mechanism 634 to proceed obliquely toward the front after being led out from the treating instrument outlet opening 639.

When assembling the ultrasound inspection apparatus 630 onto the endoscope 1, the rotational position of the ultrasonic scanning mechanism 634 in the insertion unit 602 is restricted. Since the observing window 638 and the illuminating widow 637 are bored in the end-face guide portion 635 in the endoscope connecting mechanism 633 so as to be inserted with the lens barrel 617 forming the observing means 612, the lens barrel forming the illuminating means, and the pipe 622 of the fluid supplying means 614, these members serve as positioning means so that the body unit 631 is assembled onto the insertion unit 602 in a precisely adjusted state in the rotational direction relative thereto.

What is claimed is:

1. An ultrasound inspection apparatus detachably connected to an endoscope, said ultrasound inspection apparatus comprising:
   an ultrasonic scanning portion having an ultrasound transducer attached thereto in the front end side for performing ultrasonic scanning by arranging transducer chips in an array arrangement;
   an endoscope-placing portion disposed at a base side position of said ultrasonic scanning portion to be detachably mounted onto an outer periphery of a distal end portion of an insertion unit of an endoscope;
   an endoscope-fixing portion for detachably fixing said distal end portion placed on said endoscope-placing portion; and
   a signal cable formed of a predetermined number of wires connected to said ultrasound transducer from the base end position of said endoscope-placing portion and extending along the exterior of said insertion unit.

2. An ultrasound inspection apparatus according to claim 1, further comprising a guide portion disposed between said ultrasonic scanning portion and the endoscope-placing portion, wherein said guide portion has a guide groove communicated with a treating instrument guide channel formed in said distal end portion, said guide groove for guiding a treating instrument led out from said treating instrument guide channel toward a scanning region of said ultrasound transducer.

3. An ultrasound inspection apparatus according to claim 2, wherein ultrasound beams emitted from said ultrasound transducer is arranged at a position crossing at least part of a passage for said treating instrument.

4. An ultrasound inspection apparatus according to claim 3, wherein when said ultrasound inspection apparatus is attached to said insertion unit, said ultrasonic scanning portion is arranged in a position lower than said angle portion while a emitting and receiving surface of said ultrasound transducer faces in a direction orthogonal to the center line of vertical curving direction of said angle portion, and wherein said endoscope-placing portion is provided with a portion for positioning said distal end portion of said insertion unit in the circumferential direction of said distal end portion.

5. An ultrasound inspection apparatus according to claim 1, further comprising a guide pipe disposed between said ultrasonic scanning portion and said endoscope-placing portion, wherein said guide pipe is connected to a treating instrument guide channel formed in said distal end portion, said guide pipe for guiding a treating instrument being led out from said treating instrument guide channel toward a scanning region of said ultrasound transducer, and said guide pipe being formed to be insertable into said treating instrument guide channel by a predetermined length.

6. An ultrasound inspection apparatus according to claim 1, wherein a front surface inclined downwardly toward the front is formed in said distal end portion of said endoscope-placing portion and said ultrasonic scanning portion is arranged solely on said front inclined surface.

7. An ultrasound inspection apparatus according to claim 1, wherein said endoscope-fixing portion is formed of curved elastic plate pieces arranged with both lateral ends of said endoscope-placing portion, said elastic plate pieces embracing of said distal end portion.

8. An ultrasound inspection apparatus according to claim 1, wherein a body unit is formed as one body of said ultrasonic scanning portion and said endoscope-placing portion, and wherein said endoscope-fixing portion is formed of an elastic ring to be detachably coupled to said body unit to said distal end portion of said endoscope.

9. An ultrasound inspection apparatus according to claim 1, wherein said endoscope-fixing portion is formed of a closed loop shaped ring portion arranged with said endoscope-placing portion.

10. An ultrasound inspection apparatus according to claims 7 or 9, wherein said endoscope-placing portion is provided with an extending portion for said signal cable, said extending portion rising obliquely toward said base end of said endoscope-fixing portion.

11. An ultrasound inspection apparatus according to claim 1, wherein said signal cable has a flat cross-section and is placed so as to face in a direction orthogonal to a one curving direction of said angle portion at least in a position along said angle portion.

12. An ultrasound inspection apparatus according to claim 1, wherein two of said signal cables are led out from said endoscope-placing portion at substantially symmetrical positions relative to the center line of one curving direction of said angle portion at least in a position along said angle portion.

13. An ultrasound inspection apparatus according to claim 10, wherein said two of said signal cables join into one at a position passing through said angle portion.

14. An ultrasound inspection apparatus detachably connected to an endoscope, said ultrasound inspection apparatus being attached to said endoscope for performing electronic ultrasonic scanning interchangeably with an end cap attached to a distal end portion forming an insertion unit of said endoscope so as to cover the front end face of said distal end portion, said end cap having a nozzle for spraying washing fluid toward an observing window, said ultrasound inspection apparatus comprising:

an endoscope connecting mechanism formed of an end cover for covering the front face of said insertion unit and having a nozzle attached to the outer surface thereof, and a peripheral barrel arranged with said end cover for covering the outer peripheral portion of said distal end portion; and an ultrasonic scanning mechanism protruding from said end cover toward the front and having an ultrasound transducer attached thereto for performing ultrasonic scanning by arranging transducer chips in an array arrangement.

15. An ultrasound inspection apparatus according to claim 14, wherein said ultrasonic scanning mechanism has a planar or convex-curved inclined surface slanting downward from said end cover toward the front, and said transducer chips forming said ultrasound transducer are arranged on the inclined surface toward the inclining direction.

16. An ultrasound inspection apparatus according to claim 14, wherein said endoscope connecting mechanism is provided with fixing means formed on the outer surface of a peripheral barrel thereof for detachably fixing said endoscope connecting mechanism on the outer peripheral surface of said distal end portion of said insertion unit.

* * * * *

UNITED STATES PATENT AND TRADEMARK OFFICE
CERTIFICATE OF CORRECTION

PATENT NO.    : 6,461,304 B1                                        Page 1 of 1
DATED         : October 8, 2002
INVENTOR(S)   : Tanaka et al.

It is certified that error appears in the above-identified patent and that said Letters Patent is hereby corrected as shown below:

<u>Title page, Item [54] and Column 1, lines 1-3,</u>
Title should read: -- ULTRASOUND INSPECTION APPARATUS DETACHABLY CONNECTED TO AN ENDOSCOPE --
Item [30], Foreign Application Priority Data should read:
-- [30]        Foreign Application Priority Data
Sep. 22, 1999    (JP) ..................................... 11-268251
Sep. 24, 1999    (JP) ..................................... 11-270323
Sep. 27, 1999    (JP) ..................................... 11-271688
Sep. 28, 1999    (JP) ..................................... 11-273624
Sep. 30, 1999    (JP) ..................................... 11-278193 --

Signed and Sealed this

Twenty-first Day of January, 2003

JAMES E. ROGAN
*Director of the United States Patent and Trademark Office*